United States Patent [19]
Lewis et al.

[11] Patent Number: 5,994,099
[45] Date of Patent: Nov. 30, 1999

[54] EXTREMELY ELASTIC SPIDER SILK PROTEIN AND DNA CODING THEREFOR

[75] Inventors: Randolph V. Lewis; Cheryl Y. Hayashi, both of Laramie, Wyo.

[73] Assignee: The University of Wyoming, Laramie, Wyo.

[21] Appl. No.: 09/010,928

[22] Filed: Jan. 22, 1998

Related U.S. Application Data

[60] Provisional application No. 60/070,094, Dec. 31, 1997.
[51] Int. Cl.[6] ............................. C12P 21/06; C12N 15/00; C07H 17/00; C07K 14/00
[52] U.S. Cl. ..................... 435/69.1; 435/320.1; 435/325; 435/252.3; 536/23.1; 530/350
[58] Field of Search ................................. 435/69.1, 320.1, 435/325, 252.3; 536/23.1; 530/350

[56] References Cited

PUBLICATIONS

C. Hayashi et al., Evidence from Flagelliform Silk cDNA for the Structural Basis of Elasticity and Modular Nature of Spider Silks, *J. Mol. Biol.*, vol. 275, pp. 773–784 (1998).
M. Xu et al., Structure of a Protein Superfiber: Spider Dragline Silk, *Proc. Natl. Acad. Sci. USA*, vol. 87, pp. 7120–7124 (1990).
M. B. Hinman et al., Isolation of a Clone Encoding a Second Dragline Silk Fibrion, *J. Biol. Chem.*, vol. 267, No. 27, pp. 19320–19324 (1992).
A. Simmons et al., Molecular Orientation and Two–Component Nature of the Crystalline Fraction of Spider Dragline Silk, *Science*, vol. 271, pp. 84–87 (1996).
J. Kummerlen et al., Local Structure in Spider Dragline Silk Investigated by Two–Dimensional Spin–Diffusion Nuclear Magnetic Resonance, *Macromolecules*, vol. 29, pp. 2920–2928 (1996).

S. L. Stauffer et al., Comparison of Physical Properties of Three Silks from *Nephilia Clavipes* and a*Araneus Gemmoides*, *The Journal of Arachnology*, vol. 22, pp. 5–11 (1994).
K. Mita et al., Highly Repetitive Structure and its Organization of the Silk Fibroin Gene, *J. Mol. Evol.*, vol. 38, pp. 583–592 (1994).
F. Vollrath et al., Modulation of the Mechanical Properties of Spider Silk by Coating with Water, *Nature*, vol. 340 pp. 305–307, (1989).
T. Kohler et al., Thread Biomechanics in the Two Orb–Weaving Spiders *Araneus Diadematus* . . . and *Uloborus Walckenaerius* . . . , *Journal of Experimental Zoology*, vol. 271, pp. 1–17 (1995).
Paul A. Guerette et al., Silk Properties Determined by Gland–Specific Expression of a Spider Fibroin Gene Family, *Science* vol. 272, pp. 112–115 (1996).
J. P. O'Brien et al., Design, Synthesis, and Fabrication of a Novel Self–Assembling Fibrillar Protein, *Am. Chem. Soc., ACS Symposium Series 554*, pp. 105–117 (1994).

*Primary Examiner*—Karen Cochrane Carlson
*Attorney, Agent, or Firm*—Birch, Stewart, Kolasch & Birch, LLP

[57] ABSTRACT

Cloned DNA encoding spider flagelliform silk proteins described. The translated amino acid sequence of the cloned cDNA shows that the flagelliform silk protein is composed largely of repeated motifs. The dominant motif of this protein is Gly-Pro-Gly-Gly-X, which can appear up to 63 times in tandem arrays. This motif likely forms Pro[2]-Gly[3] type II β-turns. The resulting series of concatenated β-turns are thought to form a helix (β-spiral). The present inventors propose that this spring-like β-spiral is the basis of the elasticity of silk.

71 Claims, 9 Drawing Sheets

FIG.1

N-TERMINAL REGION

```
  1 CGCTT GCTTT ACCTC GGCAG TGATA TTTCT TTTCT TAGCG CAGTG TGCGT

51 CGACG TACGG AAGGG GGATT ATAGC CAACT CCCCT TTCTC AAACC CTAAC

101 ACAGC GGAAA GCTTT TGCAC GATCT TTCGT GAGCA ATATT GTTTC TAGTG

151 GAGAA TTTGG AGCCC AAGGA GCCGA AGACT TCGAT GACAT AATTC AGAGT

201 CTCAT ACAGG CCCAG  AGC  |ATG| GGC AAA GGG CGG CAT GAT ACG AAG
                           |Met| Gly Lys Gly Arg His Asp Thr Lys
246 GCC AAG GCG AAA GCG ATG CAG GTA GCC CTT GCT TCT TCT ATA GCC
    Ala Lys Ala Lys Ala Met Gln Val Ala Leu Ala Ser Ser Ile Ala
291 GAA TTG GTT ATT GCA|GAA AGC AGC GGA GGC GAT GTG CAA CGC AAA
    Glu Leu Val Ile Ala▼Glu Ser Ser Gly Gly Asp Val Gln Arg Lys
336 ACC AAC GTT ATC TCC AAC GCT TTG AGA AAC GCC TTG ATG TCT ACA
    Thr Asn Val Ile Ser Asn Ala Leu Arg Asn Ala Leu Met Ser Thr
381 ACA GGC AGC CCA AAC GAA GAG TTC GTC CAT GAA GTT CAA GAC CTC
    Thr Gly Ser Pro Asn Glu Glu Phe Val His Glu Val Gln Asp Leu
426 ATC CAG ATG TTA TCT CAA GAA CAG ATC AAC GAG GTA GAT ACT TCA
    Ile Gln Met Leu Ser Gln Glu Gln Ile Asn Glu Val Asp Thr Ser
471 GGA CCA GGG CAG TAC TAC AGG TCG TCT TCT TCC GGT GGA GGA GGT
    Gly Pro Gly Gln Tyr Tyr Arg Ser Ser Ser Ser Gly Gly Gly Gly
516 GGA GGA CAA GGA GGT CCT GTA GTT ACT GAA ACA CTG ACC GTT ACA
    Gly Gly Gln Gly Gly Pro Val Val Thr Glu Thr Leu Thr Val Thr
561 GTT GGC GGA TCC GGT GGA GGG CAA CCT TCA GGT GCA
    Val Gly Gly Ser Gly Gly Gly Gln Pro Ser Gly Ala
```

FIG.2

SPACER MOTIF

FIG.3A  a. AMINO ACIDS

```
v.1  TIVEDLDITIDGADGPITISEELTIGGA
     ||  ||||||||||||||||||||  ||
v.2  TIIEDLDITIDGADGPITISEELTISGA
     ||  |||||||||||||||||||||||
v.3  TITEDLDITIDGADGPITISEELTISGA
```

FIG.3B  b. NUCLEOTIDES

```
v.1  ACAATCGTAGAGGATTTGGATATTACAATTGATGGTGCAGAT
     ||||||  ||||  ||  |||||||||||||||||||  |||
v.2  ACAATCATAGAAGACTTGGATATTACAATTGATGGCGCTGAT
     ||||||  ||||||||||||||||||||||||||||||  |||
v.3  ACAATCACCGAAGACTTGGATATTACAATTGATGGCGCAGAT
```

```
v.1  GGCCCGATAACAATATCAGAAGAATTAACAATCGGTGGAGCA
     ||||||||||  ||  ||||||||||||||||||  ||||  ||
v.2  GGCCCGATAACGATTTCAGAAGAATTAACAATTAGTGGTGCT
     ||||||||||||||||||||||||||||||||||||||||||
v.3  GGCCCGATAACGATTTCAGAAGAATTAACAATTAGTGGTGCT
```

FLAG REPEATS

INDIVIDUAL MOTIFS

☐ Gly-Pro-Gly-Gly-X   ▦ Gly-Gly-X   ■ spacer

ENSEMBLE REPEAT

FIG.5A

C-TERMINAL REGIONS

ALIGNMENT

```
        1
Flag    SR----------VPDMV-NGIMSA-MQGSGFNYQMFGNMLSQYSSGSGTCNP--
MaSp1   SRLSSPQASSRVSSAVSNLVASG-PTNSAALSSTISNVVSQ----IGASNPGL
MaSp2   SRLASPDSGARVASAVSNLVSSG-PTSSAALSSVISNAVSQ----IGASNPGL
ABF-1   ?????????RVSSAVSSLVSSG-PTTPAALSNTISSAVSQ----ISASNPGL
ADF-1   NRLSSAGAASRVSSNVAAIASAG----AAALPNVISNIYSQ----VLSS--GV
ADF-2   SRLSSPSAAARVSSAVS-LVSNGGPTSPAALSSSISNVVSQ----ISASNPGL
ADF-3   SRLSSPAASSRVSSAVSSLVSSG-PTKHAALSNTISSVVSQ----VSASNPGL
ADF-4   SVYLRLQPRLEVSSAVSSLVSSG-PTNGAAVSGALNSLVSQ----ISASNPGL
         LSSPAASSR 54
Flag    NNVNVLMDALLAALHCLSNH-GSSSFAPSPTPAAMSAYSNSVG--RMFAY--*
MaSp1   SGCDVLIQALLEVVSALIQILGSSSIGQVNYGSAGQATQI-VGQSVYQAL-G*
MaSp2   SGCDVLIQALLEIVSACVTILSSSSIGQVNYGAASQFAQV-VGQSVLSAF--*
ABF-1   SGCDVLVQALLEVVSALVHILGSSSVGQINYGASAQYAQM-V??????????
ADF-1   SSSEALIQALLEVISALIHVLGSASIGNVSSVGVNSALNA-V-QNAVGAYAG*
ADF-2   SGCDILVQALLEIISALVHILGSANIGPVNSSSAGQSASI-VGQSVYRALS-*
ADF-3   SGCDVLVQALLEVVSALVSILGSSSIGQINYGASAQYTQM-VGQSVAQALA-*
ADF-4   SGCDALVQALLELVSALVAILSSASIGQVNVSSVSQSTQM-ISQ----ALS-*
```

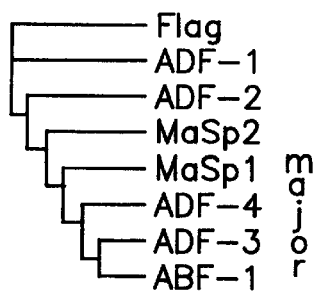

FIG.5B

AMINO ACIDS

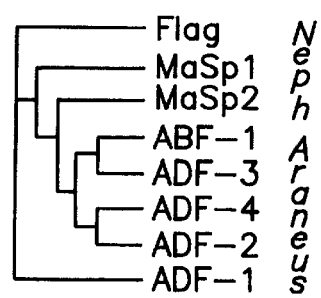

FIG.5C

NUCLEOTIDES

SPIDER SILK MODULES

FIG. 8A

Arrangement of Modules Within Spider Silk Proteins

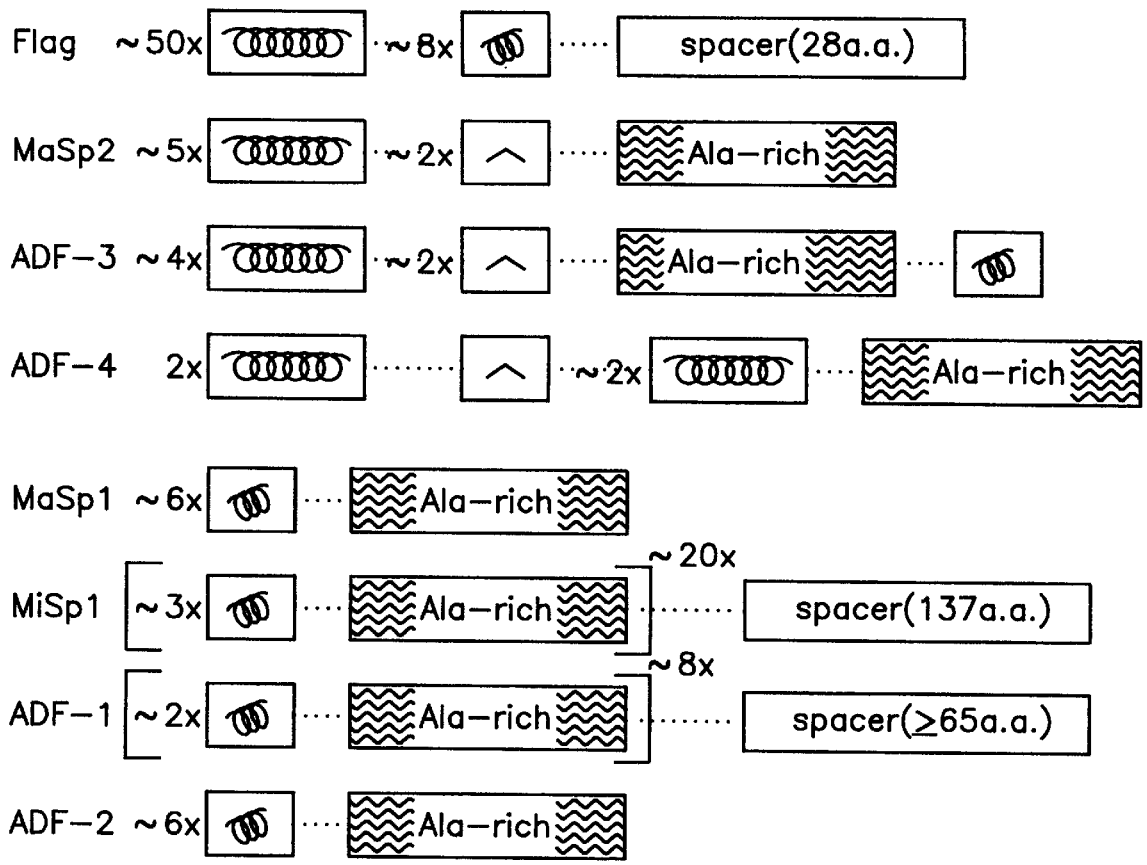

FIG. 8B

- GPGXX repeats form a β-spiral that confers *elasticity*
- GGX repeats form a $3_{10}$-helix that alters chain direction
- GPX are linker sequences that form transitions between different modules
- Ala-rich forms β-sheets that provide strengthening *crystalline* regions
- SPACER regions disrupt glycine/alanine rich sequences

EXTREMELY ELASTIC SPIDER SILK PROTEIN AND DNA CODING THEREFOR

The present application claims priority under 35 USC § 119(e) of Provisional Application Ser. No. 60/070,094 titled: "Extremely Elastic Spider Silk Protein and DNA Coding Therefor" filed on Dec. 31, 1997, inventors: Randolph V. Lewis and Cheryl Y. Hayashi, Attorney Docket No. 1447-108P, the entire contents of which are incorporated herein by reference.

TECHNICAL FIELD

The present invention relates to polypeptides that form macroscopic fibers and to cloned DNA encoding such polypeptides. Preferred embodiments of the present invention are those silk proteins made in the flagelliform glands of the spider *Nephila clavipes* and DNA encoding these proteins. The silks of the present invention also encompass fibers made from synthetic polypeptides of amino acid sequences derivable from the amino acid sequence of the *N. clavipes* flagelliform silks or made from polypeptides expressed from cloned DNA obtained from a library of spider complementary or genomic DNA.

BACKGROUND ART

Spider silks are an ideal system for exploiting the relationship between protein design and function. While silk production has evolved multiple times within arthropods, silk use is most highly developed in spiders. Spiders are unique both in their dependence on and ability to spin an array of silk proteins throughout their lifetimes. Each type of silk is secreted and stored by a different type of abdominal gland until extruded by tiny spigots on the spinnerets. These proteins are used singly or in combinations for draglines, retreats, egg sacs, or prey-catching snares. Given these specialized ecological roles, individual silks appear to have mechanical properties that correspond to their individual functions.

Most molecular and structural investigations on spider silks have focused on dragline silk and its extreme toughness (e.g. Xu & Lewis, *Proc. Natl. Acad. Sci., USA* 87, 7120–7124, 1990; Hinman & Lewis, *J. Biol. Chem.* 267, 19320–19324, 1992; Thiel et al., *Biopolymers* 34, 1089–1097, 1994; Simmons et al., *Science* 271, 84–87, 1996; Kümmerlen et al., *Macromol.* 29, 2920–2928, 1996; and Osaki, *Nature* 384, 419, 1996). Dragline silk, often referred to as major ampullate silk because it is produced in the major ampullate glands, has a tensile strength ($5 \times 10^9$ $Nm^{-2}$) similar to Kevlar ($4 \times 10^9$ $Nm^{-2}$) (Gosline et al., *Endeavour* 10, 37–43, 1986; Stauffer et al., *J. Arachnol.* 22, 5–11, 1994). In addition to this exceptional strength, dragline silk also exhibits ~35% elasticity (Gosline et al., *Endeavour* 10, 37–43, 1986). Thus a structure/function understanding of dragline silk must account for both strength and elasticity.

Silk strength is widely attributed to crystalline β-sheet structures. Such protein domains are found in both lepidopteran silks (e.g. *Bombyx mori*, Mita et al., *J. Mol. Evol.* 38, 583–592, 1994) and spider silks (Xu & Lewis, *Proc. Natl. Acad. Sci., USA* 87, 7120–7124, 1990; Hinman & Lewis, *J. Biol. Chem.* 267, 19320–19324, 1992; Gosline et al., *Endeavour* 10, 37–43, 1986). In contrast, elasticity is generally thought to involve amorphous regions (Wainwright et al., *Mechanical design in organisms*, Princeton University Press, Princeton, 1982). More precise characterization of these amorphous components can be revealed by molecular sequence data.

Based on the protein sequences of major ampullate silk proteins, a β-turn structure was suggested to be the likely mechanism of elasticity (Hinman & Lewis, *J. Biol. Chem.* 267, 19320–19324, 1992). However, assessing this proposition was problematic because dragline silk is a hybrid of at least two distinctive proteins which must impart both strength and moderate elasticity.

To elucidate the basis of silk elasticity, the present inventors have cloned a component of the stretchiest of silks; the capture spiral of an orb-web. The capture thread has a lower tensile strength ($1 \times 10^9$ $Nm^{-2}$) but several times the elasticity (>200%) of dragline silk (Vollrath & Edmonds, *Nature* 340, 305–307, 1989; Köhler & Vollrath, *J. Exp. Zool.* 271, 1–17, 1995). The capture spiral is formed from both flagelliform and aggregate gland silks. However, the present inventors focused on flagelliform silk because it is the core fiber of the spiral while aggregate silk provides a non-fibrous, aqueous coating. Thus, while aggregate silk is an integral part of the elastic capture spiral, it is flagelliform silk that must actually stretch. The present inventors report the cloning of substantial cDNA for this silk protein.

DISCLOSURE OF THE INVENTION

Silk fibers can be made from synthetic polypeptides having amino acid sequences substantially similar to the repeat units of a silk protein or from polypeptides expressed from cloned DNA encoding a natural or engineered silk protein.

Thus, it is one object of the present invention to provide cloned DNA that encodes a spider silk protein or a substantial portion of a spider silk protein. The cloned DNA is preferably obtained from an orb web spider (*Nephila clavipes*). Cloned cDNA from the flagelliform gland of, *Nephila clavipes* is described in detail below.

As will become evident, naturally occurring spider silk proteins comprise an imperfectly repetitive structure. However, the imperfection in the repetition is likely to be a consequence of the process by which the silk protein genes evolved, rather than a requirement for fiber formation. The imperfection in repetition is thus likely to only subtly affect the characteristics of the fibers, which form from the aggregation of the protein molecules.

Accordingly, it is a second object of the present invention to provide cloned DNA encoding an engineered spider silk protein comprising a polypeptide having direct repeats of a unit amino acid sequence. Alternatively, the cDNA may include several different unit amino acid sequences to form a "copolymer" silk protein and especially a "block copolymer" silk protein.

It is a third object of the invention to provide a spider silk protein expressed from a cloned DNA, wherein the cloned DNA is either one obtained from a spider flagelliform gland cDNA, a genomic DNA, or synthetic DNA.

Finally, it is an additional object of the present invention to provide fibers made from silk protein obtained by expression of cloned DNA or by other synthetic methods.

The present invention will also serve to give insight into the flagelliform protein structure thereby furthering the understanding of the relationship between silk protein structure and fiber elasticity, tensile strength and self-assembly.

ABBREVIATIONS

The following represent abbreviations used in the present application:
Silk genes from *Nephila clavipes*: Flag=flagelliform fibroin MaSp1=major ampullate spidroin 1 (Xu & Lewis, *Proc. Natl. Acad. Sci., USA* 87, 7120–7124, 1990)

MaSp2=major ampullate spidroin 2 (Hinman & Lewis, *J. Biol. Chem.* 267, 19320–19324, 1992)

Silk genes from Araneus diadematus:

ADF-1=fibroin 1,

ADF-2=fibroin 2,

ADF-3=fibroin 3, and

ADF-4=fibroin 4 (all Guerette et al., *Science* 272, 112–115, 1996)

C-terminal sequence from *Araneus bicentenarius*: ABF-1 (Beckwitt & Arcidiacono, *J. Biol. Chem.* 269, 6661–6663, 1994) Phylogenetic tree descriptors:

CI=consistency index excluding uninformative characters (Kluge & Farris, *Syst. Zool.* 40, 117–130, 1969), and RI=retention index (Farris, *Cladistics* 5, 417–419, 1989)

BRIEF DESCRIPTION OF THE DRAWINGS

FIG. 1. (SEQ ID NO:1, residues 1-596) Nucleotide sequence of 5' end of Flag cDNA. Flag5' includes a putative start codon which is highlighted by a box. An arrow indicates a possible cleavage site. The open reading frame was unambiguously determined by the lack of stop codons throughout 2,611 basepairs of Flag5' sequence.

FIG. 2. The translated Flag5' (SEQ ID NO:28) and Flag3' (Flag=SEQ ID NO: 4, residues 821–907; MaSp1=SEQ ID NO: 20; MaSp2=SEQ ID NO: 21; ABF-1=SEQ ID NO: 22; ADF-1=SEQ ID NO: 23; ADF-2=SEQ ID NO: 24; ADF-3=SEQ ID NO: 25; ADF-4=SEQ ID NO: 26; possible frame shift in ADF-4=SEQ ID NO: 27) sequences. Glycine is indicated by an open oval and proline is indicated by a black oval. Other amino acids are shown by the standard one-letter abbreviations.

FIG. 3. The flagelliform spacer regions are aligned by (a) amino acids and (b) nucleotides. Version (v.) 1 (SEQ.ID.NO.:14, 15) is from Flag5' and v.2 (SEQ.ID.NO.:16, 17) and v.3 (SEQ.ID.NO.:18, 19) are from Flag3'.

FIG. 5(a). One possible alignment of the translated conserved C-terminal regions of spider silk genes. ABF-1 omits sequence (?) at the beginning and end because it is based on a PCR amplification product. Stop codons are shown by *. Residues shared by more than half the sequences in a given position are shown in bold. The boxed region shows a possible frame shift in ADF-4. The effects of a minor alteration in DNA sequence are shown in the lower half of the box.

FIG. 5(b). The shortest parsimony tree for the aligned amino acids (length=186, CI=0.79, RI=0.51, rooted with Flag). Unit costs were assumed between any two amino acids. Gaps were counted as missing. (c) The shortest parsimony network for the aligned DNA sequences (length= 499, CI=0.68, RI=0.36). Transitions and transversions were weighted equally. Gaps were counted as missing. Alignment was done according to amino acids but included the minor alteration in ADF-4 nucleotide sequence described on page 24.

FIG. 8(a). Arrangement of Modules within various spider silk proteins. These proteins include Flag (according to the present invention), ADF-1, ADF-2, ADF-3, ADF-4, MiSp1, MaSp1, and MaSp2.

FIG. 8(b). Function of modules. FIG. 8(b) provides a representation of the functional and structural characteristics of the modules displayed in FIG. 8(a).

BEST MODE FOR CARRYING OUT THE INVENTION

Figure 4:
FIG. 4. The INDIVIDUAL flagelliform motifs are organized into a higher-level ENSEMBLE repeating unit. Based on the lengths of the higher-level repeat and flagelliform silk mRNA, approximately 14 ensemble repeats typically occur in each individual protein monomer.

Like all silk proteins, the flagelliform protein is composed largely of repeated motifs. The dominant motif of this protein is Gly-Pro-Gly-Gly-X (SEQ ID NO:29), which can appear up to 63 times in tandem arrays in the natural protein. This motif, like the sequence $Pro^2$-$Gly^3$ likely forms type II β-turns. The resulting series of concatenated β-turns are thought to form a helix (β-spiral). This glycine and proline rich region which forms a β-spiral is sometimes referred to herein as a βs region. Without being bound by any theory of the invention, the present inventors propose that this spring-like β-spiral is the basis of the elasticity of flagelliform silk.

The variable fifth position of the motif (X) is occupied by a small subset of residues (Ala, Ser, Tyr, Val). Moreover, these X amino acids occur in specific patterns throughout the repeats. This patterned variation strongly suggests that with hydration, the β-spirals form hydrogen bonded networks that increase the elasticity of flagelliform silk. The self-assembly of flagelliform protein monomers into silk fibers may be promoted by β-spiral/β-spiral interactions.

In addition to the Gly-Pro-Gly-Gly-X motif, there are two other motifs in the flagelliform protein; Gly-Gly-X and a non-silk like "spacer", sometimes referred to herein as a Gr (Glycine rich) and a S region, respectively. It is felt that these additional two motifs may contribute to the alignment of monomers into fibers. These types of orienting mechanisms are significant because the flagelliform protein is the first spider silk known to lack poly-alanine regions. Poly-alanine regions provide for β-sheet formation between neighboring protein monomers. As it lacks such regions, flagelliform silk must involve alternative assembly methods.

The flagelliform protein cDNA was compared to the other members of the spider silk gene family. The present inventors show that all spider silk proteins can be characterized as sets of shared structural modules. Generally, in any one silk protein the structure of each type of module present is well conserved. The flagelliform protein is an exception; there can be a fair degree of variation in amino acid sequence between any two examples of the same module in a single flagelliform monomer.

The polypeptides of the present invention can be made by direct synthesis or by expression from cloned DNA. The means for expressing cloned DNA are generally known in the art. However, there are some considerations for design of expression vectors that are unusual for expressing DNA encoding the spider silk proteins of the present invention.

First, the proteins are highly repetitive in their structure. Accordingly, cloned DNA should be propagated and expressed in host cell strains that will maintain repetitive sequences in extrachromosomal elements (e.g. SURE™ cells, Stratagene). Also, due to the high content of specific amino acids, it might be advantageous to use a host cell that overexpresses tRNA for these amino acids.

The proteins of the present invention can otherwise be expressed using vectors providing for high level transcription, fusion proteins allowing affinity purification through an epitope tag, and the like. The hosts can be either bacterial or eukaryotic. It is considered that yeast, especially *Saccharomyces cerevisisae*, or insect cells might be advantageous eukaryotic hosts. Expression of an engineered minor ampullate silk protein is described in co-pending Ser. No. 08/458,298, filed Jun. 2, 1995, now U.S. Pat. No. 5,756,677, herein incorporated by reference. Such an approach can be used to express proteins of the present invention.

Fibrillar aggregates will form from solutions by spontaneous self-assembly of spider silk proteins when the protein concentration exceeds a critical value. The aggregates can be gathered and mechanically spun into macroscopic fibers according to the method of O'Brien et al. [I. O'Brien et al., "Design, Synthesis and Fabrication of Novel Self-Assembling Fibrillar Proteins", in *Silk Polymers: Materials Science and Biotechnology*, pp. 104–117, Kaplan, Adams, Farmer and Viney, eds., c. 1994 by American Chemical Society, Washington, D.C.].

Specifically Exemplified Polypeptides

The present invention relates to polypeptides comprising the sequences exemplified in SEQ ID NOS. 2, 4, 5, 7 and 9. The polypeptide can be prepared by isolation from natural sources, polypeptide synthesis by known synthetic methods, expression and recovery from a recombinant organism or by any other convenient method.

A polypeptide usable in the present invention has a molecular weight in the range of 50,000 to 1,000,000 Da, preferably 75,000 to 600,000 Da, more preferably 90,000 to 500,000 Da, 450,000 to 500,000 Da.

Variants of Polypeptide

Variants of the specifically exemplified polypeptides are also encompassed by the present invention. The variants may have substantially the same characteristics as the natural polypeptides. Some possible variations are discussed below.

Substitutions, Additions and Deletions

As possible variants of the above specifically exemplified polypeptides, the polypeptide may have additional individual amino acids or amino acid sequences inserted into the polypeptide in the middle thereof and/or at the N-terminal and/or C-terminal ends thereof so long as the polypeptide possesses the desired physical and/or biological characteristics. Likewise, some of the amino acids or amino acid sequences may be deleted from the polypeptide so long as the polypeptide possesses the desired physical characteristics. Amino acid substitutions may also be made in the sequences so long as the resulting polypeptide possesses the desired physical characteristics. Specifically, as described herein, different types of modules possess specific types of structural properties. For example, the βs region of the present invention relates to a region of amino acids forming a β-spiral region. This βs region has significant elasticity. Also, modules that have strengthening qualities are those such as Alanine rich regions. By monopolizing on these types of modules and their properties, those of skill in the art will be able to assemble sythetic combinations of modules, thereby achieving specific properties in the final protein.

Amino Acid Substitutions

The specifically exemplified polypeptides, or variants thereof, of the present invention include, but are not limited to, those containing all of the amino acid sequences substantially as described herein, including altered sequences in which functionally equivalent amino acid residues are substituted for residues within the sequence, resulting in a silent change.

One or more amino acid residues within the sequence can be substituted with another amino acid of similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The polypeptide preferably comprises one of the sequences described above or a homologous variant of said polypeptide having less than 10% conservative amino acid changes, preferably less than 5% conservative amino acid changes.

Homology at the Amino Acid Level

The variants of polypeptides contemplated herein should possess more than 75% sequence identity, preferably more than 85% sequence identity, most preferably more than 95% sequence identity, even more preferably more than 98% sequence identity to the naturally occurring and/or specifically exemplified polypeptides or fragments thereof described herein. To determine this sequence identity, two polypeptides are aligned so as to obtain a maximum match using gaps and inserts. Sequence identity is determined as the product of the number of matched amino acids divided by the number of total amino acids plus gaps and inserts, multiplied by 100.

Post-translational Modification

Also included within the scope of the present invention are polypeptides or fragments or derivatives thereof which are differentially modified during or after translation, e.g., by glycosylation, proteolytic cleavage, etc.

Fusion Polypeptides

The polypeptide of the present invention may be expressed as a fusion polypeptide or chimeric polypeptide with a second polypeptide. The second polypeptide will usually impart an additional property or characteristic to the fusion polypeptide that is not possessed by the unfused, starting polypeptide of the present invention. This can play an important role in the expression and purification of the protein according to the present invention. Specifically, secretion signals for extracellular transport, poly-histidine tags, antibody epitopes, etc for purification may be added. Also, in the spacer regions it may be possible to insert specific sequences for function such as a cell binding domain like an Arg-Gly-Asp sequence or other types of cellular signalling sequences.

Fragments of Polypeptide

Fragments of the full-length polypeptides such as proteolytic cleavage fragments, which contain at least one, and preferably all, of the above-listed physical and/or biological properties are also encompassed by the present invention.

The polypeptide or fragments or varient thereof usually has a length of at least about 400 amino acids, usually less than 4500 amino acids and preferably between 800 and 2400 amino acids. Each fragment must contain at least one set of spacer, B-spiral and helix regions.

Production of Recombinant Polypeptide

The present invention is also directed to a new polypeptide and a method for producing the polypeptide. The recombinant polypeptide should possess one or more of the above-described biological and/or physical properties.

Recombinant polypeptide can be produced by a process which comprises culturing the transformed cell or microorganism described herein under conditions which allow expression of the polypeptide, optionally recovering the thus expressed polypeptide and optionally purifying the recovered polypeptide. In processes for the synthesis of the polypeptide, DNA that encodes the polypeptide is ligated into a replicable vector (i.e., one that propagates in the host cell and is stably maintained therein), the vector is used to transform host cells, and the polypeptide is recovered from the culture. Suitable replicable vectors will be selected depending upon the particular host cell chosen. The practitioner will keep in mind the repetative nature of the proteins of the invention when selecting a host-vector system.

The polypeptide produced in this manner may be different from natural polypeptide in that it may be free of other polypeptides or materials, which occur in natural polypeptide. The polypeptide produced by recombinant techniques may also contain some small amounts of contaminating materials from the microorganism, cells and/or fermentation system in which it was produced. Such polypeptide is considered "substantially purified". Thus, the present invention is also directed to isolated or substantially purified polypeptides that are produced by recombinant DNA techniques. Specific Examples are discussed below.

Purification of Recombinant Polypeptide

Recombinant polypeptide can be recovered from cultures by lysing the cells to release recombinant polypeptide that is present inside the cells. Initially, cell debris and/or medium components can be separated by centrifugation. The remaining debris and the supernatant are then repeatedly treated with solvents in which the cell debris are soluble but in which the recombinant polypeptide is not soluble to thereby precipitate recombinant polypeptide or vice versa. These procedures can be repeated and combined with other procedures including filtration, dialysis and/or chromatography to obtain a pure product.

DNA and RNA

The DNA of the invention codes for any one of the above-described polypeptides including, but not limited to, those shown in SEQ. ID NOS. 2, 4, 5, 7 and 9, including fusion polypeptides, variants and fragments thereof. The sequence of the cDNA that has actually been sequenced is shown in SEQ. ID. NOS. 1, 3, 6 and 8. The present invention also includes cDNA as well as genomic DNA containing or comprising the requisite nucleotide sequences as well as corresponding RNA.

Degenerate Sequences

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code.

DNA Modification

Substitution, deletion or insertion of nucleotides readily modifies the DNA, thereby resulting in novel DNA sequences encoding the polypeptide or its derivatives. These modified sequences are used to produce mutant polypeptide and to directly express the polypeptide.

Hybridizable Variants

The DNA molecule can comprise a nucleotide sequence selected from the group consisting of SEQ ID NOS. 1, 3, 6 and 8, or can comprise a nucleotide sequence selected from the group consisting of a nucleotide sequence that hybridizes to a DNA molecule having these sequences or to a DNA molecule encoding any one of amino acid sequence SEQ ID NOS. 2, 4, 5, 7 and 9 under salt and temperature conditions equivalent to 6× SSC and 68° C. and that encodes a polypeptide that has one or more or all of the above-described physical and/or biological properties. The present invention also includes polypeptides coded for by these hybridizable variants.

Recombinant DNA Constructs

Recombinant DNA constructs comprising one or more of the DNA or RNA sequences described herein and an additional DNA and/or RNA sequence are also included within the scope of this invention. These recombinant DNA constructs have sequences that do not occur in nature or exist in a form that does occur in nature but exist in association with other materials that do not occur in nature. The DNA and/or RNA sequences described hereinabove are "operably linked" with other DNA and/or RNA sequences. DNA regions are operably linked when they are functionally related to each other. For example, DNA encoding a presequence or secretory leader is operably linked to DNA encoding a polypeptide if the expression product is a preprotein, which results in the secretion and maturation of the polypeptide by cleavage of the presequence. A promoter is operably linked to a coding sequence if it controls the transcription of the coding sequence; or a ribosome binding site is operably linked to a coding sequence if it is positioned so as to permit translation. Generally, operably linked means contiguous (or in close proximity to) and, in the case of coding elements of DNA, contiguous and in reading frame.

Vectors

The invention is further directed to a replicable vector containing cDNA which codes for the polypeptide and which is capable of expressing the polypeptide.

The present invention is also directed to a vector comprising a replicable vector and a DNA sequence corresponding to the above-described gene inserted into said vector. The vector may be an integrating vector. Autonomously replicating plasmids are convenient vecors. Construction strategy for some vectors of the invention is explained herein.

Chemical Modification

The protein produced according to the present invention can be chemically modified after sythesis of the polypeptide. Due to the presence of several carboxylic acid side chains (Asp or Glu) in the spacer regions, a wide variety of different chemical groups can be attached to the silk proteins. The simplest and easiest procedure is to use a water-soluble carbo-diimide to attach the modifying group via a primary amine. If the group to be attached has no primary amine a variety of linking agents can be attached via their own primary amines and then the modifying group attached via an available chemistry. Jennes, L. and Stumpf, W. E. *Neuroendocrine Peptide Methodology*, Chapter 42. P. Michael Conn, editor. Academic Press, 1989.

Desirable chemical modifications include derivatization with peptides that bind to cells, e.g. fibroblasts, derivatization with antibiotics and derivatization with cross-linking agents so that cross-linked fibers can be made. The selection of derivatizing agents for a particular purpose is within the skill of the ordinary practitioner of the art.

The following examples are provided to illustrate the invention in more detail. The examples are not to be taken as limiting the invention, the scope of which is rather defined by the claims following.

EXAMPLE 1

Isolation of Flagelliform Silk Clones

Eight flagelliform silk cDNA clones were isolated and all contained glycine-rich repetitive sequences. BLAST searches (NCBI) resulted in no matches to the database of known sequences. Seven of the inserts overlapped each other and represent the C-terminus and preceding repetitive regions. These seven sequences were combined into Flag3'. The eighth clone, Flag5', included a putative N-terminal sequence followed by the same repetitive motifs as in Flag3'. The translated sequences were consistent with the published amino acid composition of flagelliform glandular protein (Andersen, 1970), most notably in glycine and proline accounting for 64% of the residues (Table 2a,2b). Northern analyses indicated two bands of approximately 14.5 and 15.5 kb. These lengthy transcript sizes are comparable to the 12.5 kb MaSp1 mRNA (Xu & Lewis, *Proc. Natl. Acad. Sci., USA* 87, 7120–7124, 1990) and are consistent with the observed high molecular weight of electrophoresed flagelliform glandular proteins (Rodriguez & Candelas, *J. Exp. Zool.* 272, 275–280, 1995).

The unusually large transcript size (~15 kb) and pronounced guanine/cytosine bias (due to the high glycine and proline content) of the flagelliform silk gene severely limited the cDNA lengths. All other published cloning studies on spider silk genes have also reported on partial cDNAs (Xu & Lewis, *Proc. Natl. Acad. Sci., USA* 87, 7120–7124, 1990; Hinman & Lewis, *J. Biol. Chem.* 267, 19320–19324, 1992; Guerette et al., *Science* 272, 112–115, 1996). In comparison with those studies, more than twice the amount of sequence has been determined for the flagelliform gene. Yet, as discussed below, much can be inferred about the proteins encoded by these sequences. As work on the well-studied *Bombyx mori* silkworm has shown, partial cDNAs can characterize entire fibroins because silks are comprised of iterated sequences (Mita et al., *J. Mol. Biol.* 203, 917–925, 1988).

cDNA Library Construction

Flagelliform silk glands were dissected from euthanized *Nephila clavipes* (Araneae: Tetragnathidae) and flash frozen in liquid nitrogen. Total RNA was extracted from the glands and cDNA was synthesized using standard protocols with AMV reverse transcriptase followed by RNAse H and DNA polymerase I (Okayama & Berg, *Mol. Cell Biol.* 2, 161–170, 1982; Gubler & Hoffman, *Gene* 25, 263–269, 1983). Two primers were used during first strand synthesis. One primer was oligo-d(T) and the other, the hexamer WSSWSS, was based on the known high glycine content of silk proteins. The cDNA was size fractionated through a Sephacryl-1000 column and large (>1000 bp) fragments were blunt-end ligated into pGEM-3zf(+) (Promega). SURE2™ cells (Stratagene) were transformed and a library of approximately 800 recombinant colonies was constructed. Colonies were replicated on nylon membranes for screening.

Determination of Silk Clones

Eight clones with silk gene inserts were identified from the cDNA library by hybridization with the $\gamma^{32}P$ kinased probe GGWCCWGGWCAACAAGGWCCWGGW (SEQ.ID.NO.:10). This oligonucleotide was designed from a paralogous major ampullate silk sequence and reflects the high glycine and proline content of flagelliform protein (Andersen, *Comp. Biochem. Physiol.* 35, 705–711, 1970). Portions of both strands from all eight in serts were dideoxy sequenced with either SEQUENASE (Amersham) or Taq (ABI Prism). Five inserts were sequenced in their entirety by creating exonuclease III deleted clones (Henikoff, *Gene* 28, 351–359, 1984).

Northern Analysis

Flagelliform gland total RNA and RNA size markers were electrophoresed through 0.5% agarose gels (1× MOPS, 0.66M formaldehyde) and blotted. Each blot was hybridized with one of three oligonucleotide probes: CCWCCWGG-WCCNNNWCCWCCWGGWCC (SEQ.ID.NO.:11), the reverse-complement of the codons for Gly-Pro-Gly-Gly-X-Gly-Pro-Gly-Gly; the Flag5' specific ATGTTCCACCTG-TACTTCCTGGTC (SEQ.ID.NO.:12); or the Flag3' specific GCGAACATTCTTCCTACAGA (SEQ.ID.NO.:13).

Comparative Analysis

Comparisons were done with the new flagelliform sequence and all six previously published spider silk genes. These genes are expressed in four distinct types of secretory glands. Two of the genes, MaSp1 (M37137) and MaSp2 (M92913), like the flagelliform sequence, are from *Nephila* but are expressed in the major ampullate glands. The other four genes, ADF-1 (minor ampullate fibroin; U47853), ADF-2 (cylindrical gland fibroin; U47854), ADF-3 (major ampullate; U47855), and ADF-4 (major ampullate; U47856) are from *Araneus diadematus*. An additional 238 bp of only C-terminal sequence from *Araneus bicentenarius* (major ampullate; U03847) was obtained from a study using PCR (Beckwitt & Arcidiacono, *J. Biol. Chem.* 269, 6661–6663, 1994).

Phylogenetic analyses of aligned amino acid and nucleotide sequence data were performed using maximum parsimony methods. Parsimony searches were performed with PAUP v.3.1.1 (Swofford, PAUP v.3.1.1. Smithsonian Institution, Washington, D.C., 1993). The branch-and-bound option was used to find the topology requiring the fewest number of inferred evolutionary events.

The N-terminal region, repetitive region and the C-terminal region will now be characterized.

N-Terminal Region

Flag5' contains the first reported potential N-terminal sequence for any spider silk (FIG. 1). This region has a different amino acid composition and sequence from the repetitive portions of both Flag5' and Flag3'. Following this N-terminal region, the remaining Flag5' sequence proceeds without interruption into the repeats found in the rest of the protein. The only in-frame start codons are at positions 219, 261, 372, and 432. There is no earlier ATG upstream of position 219 that allows continuous translation through the rest of the sequence. Because transcription is generally initiated by the most proximal ATG (Kozak, 1984), coding likely commences at position 219.

In addition to the start codon, the 5' mRNA sequence is also likely to encode a signal peptide. Secretory signals are key elements of proteins, like spider silks (Colgin, Structure and function of minor ampullate silk proteins from *Nephila clavipes*. Ph.D. thesis, University of Wyoming, Laramie, 1996), that must be transported across the endoplasmic reticulum and secreted. There are three features of the flagelliform translation (FIG. 1) that are consistent with secretory signal sequences (Nothwehr & Gordon, *BioEssays* 12, 479–484, 1990). First, immediately following the initial methionine is a short (n) region rich with lysine, arginine, and histidine. These basic residues are exceedingly rare in the rest of the flagelliform sequence. Second, after this potential n-region, there is a hydrophobic (h) region. Third, the translated sequence was analyzed by the SignalP program (eukaryotic option—Nielsen et al., *Prot. Eng.* 10, 1–6, 1997) to identify a likely cleavage site. The glutamic acid coded by positions 306–308 had the highest score (0.340). This score was much greater than the values for the other residues (0.011 through 0.264) and approached significance (0.370). If this glutamic acid is the cleavage site, then the signal peptide would include the distinctive n- and h-regions mentioned above and be 29 amino acids in length, well within the 15–50 amino acid range of known signal sequences (Nothwehr & Gordon, *BioEssays* 12, 479–484, 1990).

Repetitive Region

Figure 2:
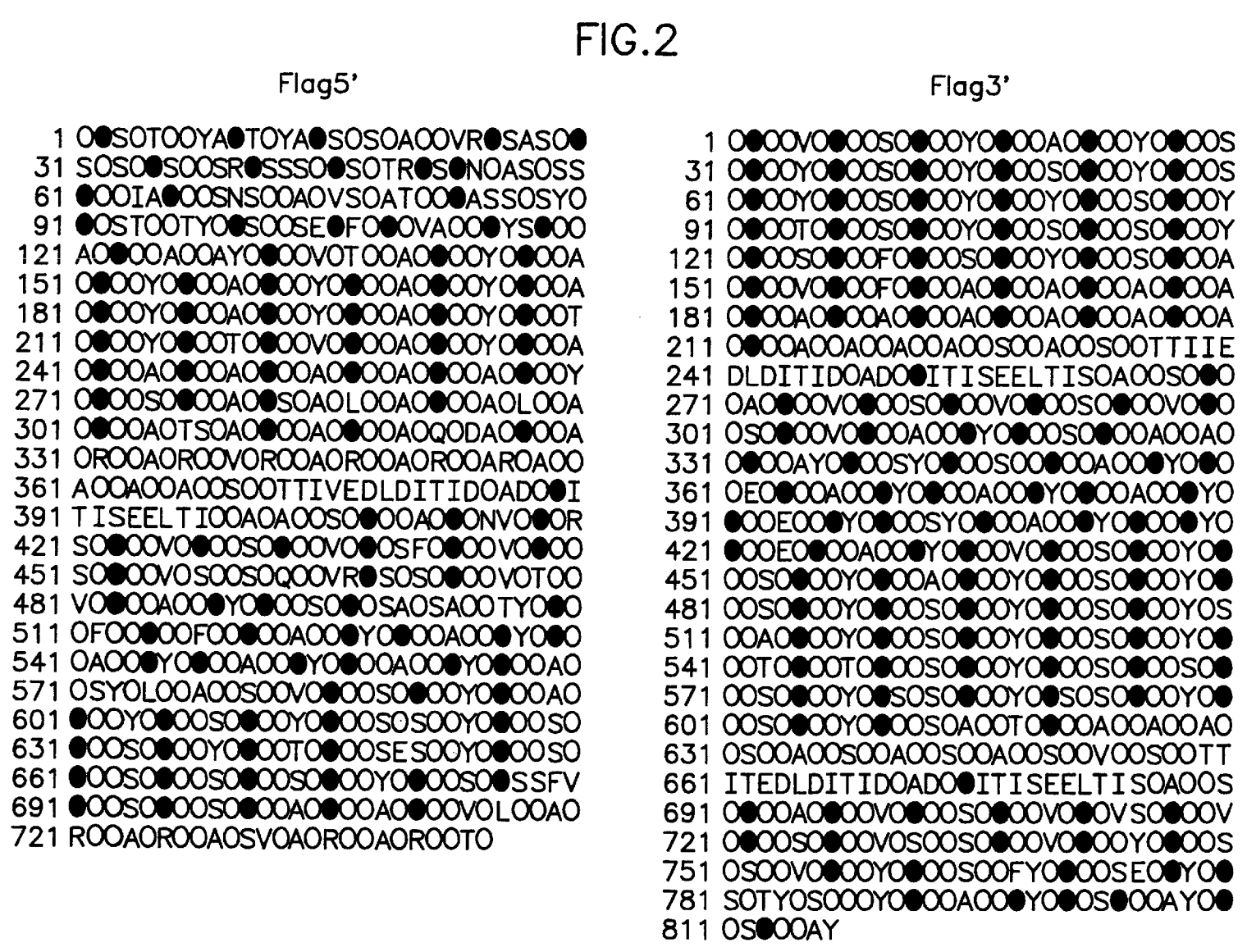

The majority of the translated flagelliform sequence is composed of glycine and proline (FIG. 2). Comparison of the Flag5' with Flag3' repetitive sequences show that they are nearly indistinguishable. Northern analyses using probes specific to sequences found in Flag5' but not Flag3' and vice-versa resulted in similar sized bands. While it is possible that the two flagelliform silk sequences are from different genes with identical functions and transcript lengths, it is more likely that Flag5' and Flag3' represent the proximal and distal ends of the same gene. All analyses of the repetitive region are based on the combined Flag5' and Flag3' sequences (=Flag). The Bombyx mori silk fibroin (Gage & Manning, *J. Mol. Biol.* 101, 327–348, 1976) and Nephila MaSp1 and MaSp2 (Hinman, unpub. data) all provide precedence for one copy of a particular silk gene per haploid genome.

The flagelliform translation product (FIG. 2) can be divided into three repetitive motifs. There are two types of glycine-rich repeating units and one non-glycine rich unit. The most common repeat is the pentapeptide Gly-Pro-Gly-Gly-X (βs region). The first four amino acids of this motif are highly conserved among the numerous individual repeats. The fifth amino acid, indicated by X, is variable. However, only a small subset of residues occupies those positions. These amino acids are preferably uncharged residues, more preferably Ala, Ser, Tyr and Val. Moreover, the distribution of the four residues among the repeats is non-random. Ala, Ser, Tyr and Val occupy up to about 95%, preferably up to about 90%, more preferably about 70 to 90% of the positions and most preferably about 90% of the X positions.

Considering the tandem repeats (Gly-Pro-Gly-Gly-X)$_i$ (Gly-Pro-Gly-Gly-X)$_{i+1}$, the following patterns are observed:
(1) if X$_i$=Ala then X$_{i+1}$ is nearly always Ala;
(2) if X$_i$=Ser then X$_{i+1}$ is usually Tyr and vice-versa; and
(3) if X$_i$=Val then X$_{i+1}$ is most likely Ser.

These preferences are reflected in the occurrence of distinct neighborhoods of Gly-Pro-Gly-Gly-X repeats. The most common region has Ser and Tyr alternating one after the other in the X positions. A variation on this pattern has Tyr replaced by Val resulting in Ser-Val alternation. The other type of neighborhood has exact repeats of Gly-Pro-Gly-Gly-Ala. In the transitions between neighborhoods, an X$^{Ser}$ motif has not been observed to follow an X$^{Ala}$ motif.

The second glycine-rich motif is the tripeptide Gly-Gly-X (Gr region). It occurs approximately tenfold fewer times than Gly-Pro-Gly-Gly-X and is present between the pentapeptide motif and the spacer, described below. The first two glycine residues are absolutely conserved with the exception of a single arginine substitution. Similar to the proline-containing motif, the X residue is predominantly alanine or serine.

Thus, the flagelliform sequence contains a series of glycine-rich motifs. Gly-Pro-Gly-Gly-X occurred 235 times (forming a βs region). Gly-Gly-X appeared 28 times (forming a Gr region). Table 1 indicates the fidelity of amino acids in each individual repeat of the overall motif.

TABLE 1

FLAG GLYCINE-RICH MOTIFS

|    | 1$^{st}$ position | 2$^{nd}$ position | 3$^{rd}$ position | 4$^{th}$ position | 5$^{th}$ position |
|----|-------------------|-------------------|-------------------|-------------------|-------------------|
| βs | 98% Gly           | 89% Pro           | 97% Gly           | 95% Gly           | 33% Ala<br>27% Ser<br>19% Tyr<br>11% Val |
| Gr | 96 Gly            | 100% Gly          | 46% Ala<br>39% Ser<br>11% Thr |         |                   |

The third repetitive flagelliform element is both the longest and rarest motif. Its three members are unmistakable amidst the sequence by their distinctive amino acid composition, particularly in being glycine poor (FIG. 2). These regions are termed "spacers" (S regions) because they disrupt the glycine and proline rich flagelliform sequence. The spacer region can be about 23 to 33 amino acids in length. However, in the native protein, they are each 28 amino acids in length. The spacers are more highly conserved than the tripeptide (Gly-Gly-X) or pentapeptide (Gly-Pro-Gly-Gly-X motifs. The spacers differ by only one or two residues from each other (FIG. 3a).

Even more dramatic than the extreme amino acid sequence conservation in the spacer sequences is the high level of nucleotide identity despite the degeneracy of the genetic code (FIG. 3b). Approximately 85% of the aligned basepairs are invariant. Of the thirteen changes, nine are silent substitutions and only four result in amino acid replacements.

Not only is the flagelliform sequence composed of individual repetitive motifs, but the motifs themselves are organized into larger ensemble repeats (FIG. 4). In the natural protein, the Gly-Pro-Gly-Gly-X motifs are tandemly arrayed greater than or equal to 43 times. They are followed by between 1 and 20 Gly-Gly-X motifs, then by at least one spacer, and finally one or more Gly-Gly-X motifs. Then, the ensemble repeat begins anew. The ensemble repeats at least one time, usually at least three times. In an engineered protein, the Gly-Pro-Gly-Gly-X element is preferably tandemly repeated 43 to 63 times, followed by 6 to 12 Gly-Gly-X elements, followed by 1 to 3, preferably 1 spacer region, followed by 1–3, preferably 1 Gly-Gly-X element.

C-Terminal Region

Following the ensemble repeats, the translated flagelliform sequence continues into a C-terminal region. This region is distinct from all the preceding sequence because of its lack of repetitive motifs, low levels of glycine and the presence of Cys, His, and Met. After 2,722 basepairs of the Flag3' open reading frame, a TAA stop codon is encountered. A polyadenylated tail is found ninety-six bases downstream of the stop codon.

The C-terminal regions of all the previously published spider silks share considerable sequence conservation and are suggested to have consensus regions common to all members of the spider silk gene family (FIG. 5a; Hinman & Lewis, 1992, supra; Beckwitt & Arcidiacono, 1994, supra; Guerette et al., 1996, supra). Six of the sequences (MaSp1, MaSp2, ABF-1, ADF-2, ADF-3, ADF-4) contain many identical residues and are trivial to align. ADF-1 corresponds well with those six after the insertion of alignment gaps. In comparison, the Flag C-terminus is exceptionally divergent.

The C-terminal sequences were aligned by amino acids with consideration of the underlying codons (FIG. 5a). In comparison to those publisheed sequences, the Flag C-terminus is exceptionally divergent. Its differing sequence and shorter length make it extremely difficult to align with the other C-termini. All possible alignments involving the Flag C-terminus are riddled with areas of dubious association because of the low sequence identity of Flag with the other silks. Given this lack of similarity, it would not have been possible to clone Flag with the C-terminal regions shared by the other spider silk genes. In contrast, six of the sequences (MaSp1, MaSp2, ABF-1, ADF-2, ADF-3, ADF-4) contain many identical residues and are trivial to align. ADF-1 corresponds well with those six after the insertion of alignment gaps. For example, the initial arginine (encoded by CGC) in Flag was aligned with the position 2 arginines (all CGN) rather than the downstream position 11 arginines (all AGR). This type of analysis, attempting to simultaneously maximize amino acid and nucleotide identities, revealed a natural frame shift or possible sequencing artifact in ADF-4. As published (Guerette et al., 1996, supra), a nine amino stretch (positions 3–11, bracketed in FIG. 5a) has 0% similarity with the corresponding region in ADF-3. However, simply inserting a gap in the nucleotide sequence (after base 951 in the Genbank entry) and deleting one base (981) from a downstream doublet of G's results in 100% similarity. Also, identity at the nucleotide level in that region more than doubles between ADF-3 and ADF-4 by incorporating the two changes. If ADF-4 does contain a natural frame shift, then amino acids 3–11 may be non-essential. Likewise, Flag has a large deletion in that same region.

The relationships among the C-terminal sequences were investigated with phylogenetic techniques. Maximum parsimony networks were computed for the aligned amino acids and nucleotides. Each analysis yielded a single tree and both trees were rooted with the divergent Flag sequence. At both the amino acid and DNA levels, Flag and ADF-1 are excluded from a group composed of the major ampullate (MaSp1, MaSp2, ABF-1, ADF-3, ADF-4) and cylindrical (ADF-2) sequences. Typical multi-gene family evolution would predict that the major ampullate C-termini are most closely related to each other regardless of spider species, contrary to the results of the DNA analysis. This contrary result of the phylogenetic analysis emphasizes the uniqueness of the Flag sequence.

Basis for the Elasticity of Spider Silk

The key structural feature of the highly elastic flagelliform silk is the dominating Gly-Pro-Gly-Gly-X motif. The present inventors propose that this motif forms type II β-turns. An exhaustive study of ~4,000 β-turns from 205 independent proteins supports $Pro^2$-$Gly^3$ as extremely likely to form a type II turn (Hutchinson & Thornton, 1994). Corroboration is provided from the well characterized mammalian W4 elastin (Urry et al., 1995) and structural studies on wheat gluten proteins (Van Dijk et al., 1997a,b). Their primary repeats (elastin Val-Pro-Gly-Val-Gly; the glutens Pro-Gly-Gln-Gly-Gln-Gln) have both been shown to form $Pro^2$-$Gly^3$ type II β-turns.

The Gly-Pro-Gly-Gly-X motif is iterated up to 63 times in the determined sequence before interruption by the Gly-Gly-X motif (FIG. 4). The resulting series of tandem β-turns likely forms a helix with each turn of the helix containing one pentapeptide motif. The present inventors have termed the resulting structure a β-spiral because of its constituent type II β-turns and to distinguish it from the recently characterized β-helix (Yoder & Jurnak, FASEB J. 9, 335–342, 1995). Upon further characterization, the silk β-spiral may be reclassified as a variant of the β-helix.

The $Pro^2$-$Gly^3$ turns usually occur in a five amino acid motif, of which four residues (i.e., GPGG) are highly invariant among individual repeats. This regularity suggests even spacing of the turns within the helical spiral. This β-spiral acts like a spring, providing elasticity to flagelliform silk. Upon stretching of the β-spiral, there is an increase in entropy between the loops. Restoration occurs by the release of the gained entropic forces as the protein resumes its more tightly folded structure.

This simple model provides for elasticity at the level of individual β-spirals. However, through inter-spiral interactions, it can simultaneously account for two crucial features of flagelliform silk: the importance of hydration and fiber self-assembly. The first attribute, hydration, is unique to flagelliform silk. Vollrath and Edmonds (1989), supra, experimentally demonstrated that hydration was necessary for the capture spiral to have its full elastomeric property. Their finding was supported by NMR spectra, which showed that water-induced mobility was a significant requirement for elasticity (Bonthrone et al., Proc. R. Soc. Lond. B 248, 141–144, 1992). Spiders naturally promote the hydration of flagelliform silk by coating it with wet, non-fibrous aggregate gland silk. Additionally, when dry, flagelliform spider silks have a much lower elasticity but a higher energy to stretch. The other fibers show no such features but major ampullate spider proteins act more like flag silk when wet but that is due to the fact that it shrinks to 50% of its original length when it gets wet.

The importance of silk hydration is consistent with the flagelliform sequence. The molecular attributes of the variable fifth residue in Gly-Pro-Gly-Gly-X imply that the elastic spiral is held together by hydrogen and hydrophobic bonds. Thus, hydration could serve two purposes. First, it stabilizes the structure by forcing hydrophobic amino acids into a packed configuration. This would tend to aggregate adjacent $X^5$=Ala spirals. But in contrast to the mammalian elastins, where hydration of the predominant hydrophobic residues generates most of the elastic force (Wasserman & Salemme, Biopolymers 29, 1613–1631, 1990; Urry et al., Ciba Found. Symp. 192, 4–30, 1995), the alanine type β-spirals alone cannot explain the elasticity of silk. Instead, much of the elasticity comes from the second, more direct role of water. By loosening the hydrogen bonds between the spirals with $X^5$=Ser/Val alternating with $X^5$=Tyr, hydration allows for more stretch with reduced breakage. The presence of such intercalated water molecules among the β-spirals is similar to the hydrogen bonded network that has been implicated in the elastic force provided by gluten proteins (Van Dijk et al., Prot. Sci. 6, 649–656, 1997).

The model of interacting β-spirals also contributes to understanding how silk protein monomers self-assemble into fibers. As discussed above with reference to elastin and glutens, bonds can form between neighboring β-spirals. Additional evidence for the likelihood of significant β-spiral interaction is provided by the bacterial virulence factor P.69 pertactin (Emsley et al., Nature 381, 90–92, 1996). The proline rich region of pertactin [(Gly-Gly-X-X-Pro)$_5$] is similar to the flagelliform silk sequence. This motif is considered important for protein-protein binding between pertactin and its target epithelial cells, much like the binding we suggest between flagelliform β-spirals. As the β-spirals associate, the silk monomers can assemble into silk fibers through a process analogous to the inter-helical hydrophobic interactions of cytoplasmic vimentin filament formation (Downing, *Proteins* 26, 472–478, 1996).

Silk assembly may be further mediated by the non-β-spiral motifs. Individual β-spirals are followed by short arrays of Gly-Gly-X motifs (FIG. 4). The (Gly-Gly-X)$_n$ domain of spider silks has been experimentally investigated with 2D spin-diffusion NMR data to best fit a $3_{10}$-helix (Kümmerlen et al., 1996, supra). This structure is consistent with $^2$H-NMR studies on dragline silk by Simmons et al. (1996), supra. Based on that data, they proposed that Gly-Gly-X stops growth in the current protein chain direction. The $3_{10}$-helices could cause such detours as they terminate the β-spiral regions.

Immediately following the $3_{10}$-helices is the spacer. While the function of the spacer remains unknown, its remarkably high sequence conservation and possession of the only negatively charged residues (Asp, Glu) among the repetitive units (FIG. 3a) suggests it is a critical component of the silk. We propose that the combination of a $3_{10}$-helix and spacer create distinct regions where flagelliform proteins can overlap and align with each other, resulting in a fiber of woven monomers. The negatively charged region of the spacer may also promote post-assembly interactions with the coating of aqueous aggregate silk.

The Modular Organization of Silk Proteins

The flagelliform sequence has implications for the general design of spider silks. If elasticity is due to Gly-Pro-Gly-Gly-X β-spirals, then with the dragline being the second most elastic silk, similar regions should be found in the major ampullate proteins. Conversely, such motifs should be absent in the inelastic minor ampullate and cylindrical silks. As expected, the only non-flagelliform silk proteins with Pro$^2$-Gly$^3$ type II β-turn sequences are the major ampullate proteins MaSp2, ADF-3, and ADF-4. These proteins contain repeats similar (Gly-Pro-Gly-Gln-Gln) or identical (Gly-Pro-Gly-Gly-Tyr) to the flagelliform Gly-Pro-Gly-Gly-X motifs. There is also a striking correspondence between the number of tandemly arrayed repeats and the mechanical properties of dragline silk compared to the capture spiral. Dragline silk, with 35% elasticity (Gosline et al., 1986, supra), has at most 9 concatenated β-turns before interruption by another motif. Flagelliform silk with the much greater 200% elasticity (Gosline et al., 1986, supra) has a minimum of 43 contiguously linked β-turns in its spring-like spirals.

Figure 6:
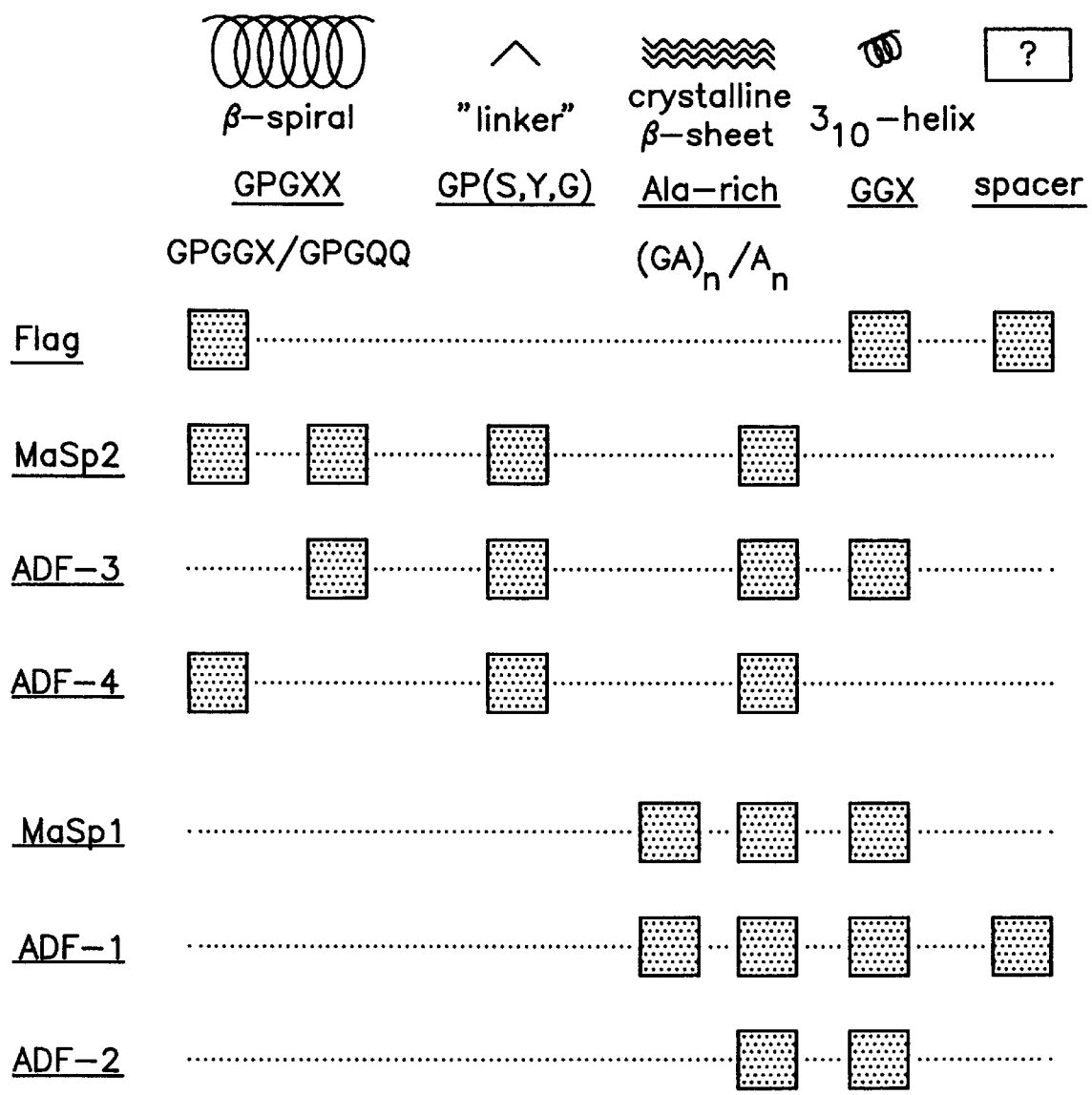
FIG. 6. The distribution of structural modules occurring within spider silks. "X" indicates a residue that may vary within or between proteins.

The similarity of Pro$^2$-Gly$^3$ type repeats in four of the seven cloned spider silks suggests that silk proteins may share other structural motifs. To investigate patterns in the occurrence of such units, the presence or absence of similar motifs (=module) was scored. Five modules were found to appear in more than one spider silk protein with no single protein having all the module types (FIG. 6).

1. GPGXX: This module confers elasticity to Flag and three of the four major ampullate proteins. This module has two types of motifs, GPGGX and GPGQQ. MaSp2 is distinctive in containing both motifs.

2. Ala-rich: This is the β-sheet crystalline module. There are two β-sheet motifs, A$_n$=poly-Ala and (GA)$_n$=Gly-Ala doublets. A$_n$ is the most common motif in all the spider silks, absent only in Flag. The two sequences with (GA)$_n$, MaSp1 and ADF-1, also have the shortest of A$_n$ stretches. Lewis (*Accts. Chem. Res.* 25, 392–398., 1992), proposed that these Ala-rich motifs form the stacked β-sheets of silks that have been observed with x-ray diffraction (Parkhe et al., *Journal of Molecular Recognition* 10, 1–6, 1997) and Fourier transform infrared spectroscopy (Dong et al., *Arch. Biochem. Biophys.* 284, 53–57, 1991). These crystalline modules are interspersed among the amorphous regions created by the glycine-rich sequences. Simmons et al. (1996), supra corroborated such a model with $^2$H NMR data and suggested that all the crystalline portions of spider silks are composed of Ala-rich sequence (contra Thiel et al., 1994, supra). The conspicuous absence of an Ala-rich module in flagelliform silk is thus entirely consistent with Bonthrone et al.'s (*Proc. R. Soc. Lond. B* 248, 141–144, 1992) silk NMR. They observed that the hydrated capture spiral is "mobile on the NMR timescale," indicating flagelliform silk has scant crystalline portions.

3. spacer: This module represents non-silk like but conserved regions that disrupt the glycine-rich repeats. In addition to the Flag spacer, we have identified a potential spacer in ADF-1. The Flag spacer clearly ends the larger ensemble repeat (FIGS. 2,4). However, the detection of the ADF-1 (minor ampullate) spacer is less obvious. Considering that ADF-1 is characterized by (GA)$_n$, (A)$_n$, and GGX, its first sixty-five residues are extremely anomalous:

HESSYAAAMAASTRNSDFIRNMSYQMGRLLSNA

GAITESTASSAASSASSTVTESIRTYGPAAIF

While this sequence is suggestive of a spacer, ADF-1 alone is too short to confirm whether a spacer motif is present in Araneus minor ampullate silk. However, new data from substantially longer Nephila cDNA verify that minor ampullate proteins contain a non-silk like but highly-conserved 137 amino acid spacer motif (Colgin, 1996, supra; Colgin & Lewis, in press, *Protein Science*.

There is no sequence or even length similarities between the spacer motifs of Flag and ADF-1. Given their lack of shared characteristics, they are likely to be of separate evolutionary origins. If they both serve as cross-over regions for fiber assembly, then this is an example of unrelated sequences converging on the same module function.

4. GP(S,Y,G): These motifs are restricted to the major ampullate proteins (MaSp2, ADF-3, ADF-4) that also contain the elasticity module. In MaSp2 and ADF-3, the GPX motifs are well conserved and regularly appear at the junctions between the GPGXX and A$_n$ motifs. Based on these characteristics, MaSp2 and ADF-3 are thought to be the more closely related of the elastic major ampullate proteins. Their GPX modules appear to serve as connecting links between flexible β-spiral and crystalline Ala-rich regions. Whether the same GPX module occurs in ADF-4 is equivocal. The individual repeats in ADF-4 do not conform well to the motif and, unlike an amorphous/crystalline bridge, their placement is decoupled from the A$_n$ motif.

5. GGX: This module has been discussed above as the chain detouring $3_{10}$-helix. It is widely distributed, occurring in Flag, ADF-3, and all three inelastic silks (MaSp1, ADF-1, ADF-2). On the basis of sequence alone, the GPX and GGX modules can be combined to yield the module 1 motif of GPGGX. Such a pathway of modular shuffling could evolve novel structural modules from pre-existing ones.

In summary, there is a modular organization, which appears to be distinct for each type of spider silk protein. The different modules and their arrangement within the spider silk proteins relates to the function and characteristic which the protein derives from the modules: the GPGGX module repeats to form a β-spiral that confers elasticity; the GGX module repeats to form a $3_{10}$-helix that alters chain direction; the GPX regions are linker sequences that form transitions between different modules; the Ala-rich regions form β-sheets that provide strengthening crystalline regions; and the spacer regions disrupt the glycine/alanine rich sequences. These types of relationships are further illustrated in FIG. 8.

The types of amino acid substitutions discussed above require further elaboration. Overall, in the present invention, amino acid substitutions are acceptable in the Ser-Thr repeat regions (ie. GPGGX$^{ser}$GPGGX$^{Thr}$..) provided that the residues remain H-bondable. Thus, Ala, Thr, Asn could be substituted for Ser with Gln, Val and Phe for Tyr. Preferably, no more than 20% of the Tyr residues are substituted. From the present sequences it appears that the Ala for Ser substitution is frequent and may lead to the same type of interactions that are apparent in the all Ala regions, with just every other residue combined with the hydrogen bonding from Tyr. Additionally, it is preferred that the GP(; region be substituted less than 20% of the time and when substituted, Ser and Ala replace Gly, and Ser, Thr and Leu replace Pro, especially prior to the spacer region. The fourth G is preferably less than 10% of the time an then to Ser or Ala.

Also, amino acid substitutions in the GPGGX$^{Ala}$ regions are not surmised to be acceptable unless all of the Ala residues are changed. If all of the Ala are changed, Val or Leu can be substituted.

Repetitions

According to the present invention, synthetic sequences can be made. These sequences use the knowledge of the different modules and the characteristics that they possess. However, certain parameters exist with respect to the number of repetitions required for a specific module to achieve a desired characteristic. For example:

a) GPGGA regions: The amount of repeats in these regions likely cannot go lower than 4 but the maximum could be higher in an artificial system where solubility can be controlled. This maximum is likely to be about 15.

b) GPGGX regions: These appear to be very flexible, therefore a number of repeats up to 50 can be used. The minimum is much harder to predict, however, 5 is a preferred lower limit.

c) Spacer regions: These regions appear no more often than every 300 amino acids nor more than 450 amino acids apart.

Likewise, it is also possible to extrapolate the types of amino acid interactions which result in the types of modules according to the present invention and postulate alternative amino acid sequences which would interact in similar manners and therefore result in the same type of characteristics.

In the past, the present inventors have disclosed sequences for various spider silk proteins. Among these are minor ampullate silk proteins (U.S. Ser. No. 08/458,298) and major ampullate silk proteins (U.S. Ser. No. 08/425,069). In these applications, it was disclosed that those of skill in the art could exploit the understanding of the relationship between structure and function of silk proteins and the fibers they make up. Specifically, certain amino acid sequences are known to impart specific properties on the final proteins. For example, the polyalanine region is known to form β-sheets thereby conferring strength to the final fiber. Also, the GPGGX motif forms a motif called a β-spiral and this motif in turn confers elasticity to the fiber. Accordingly, when interested in creating a synthetic protein (or in this case, silk fibers), one of skill in the art will now be able to exploit the qualities of the native flagelliform sequence disclosed herein in addition to the other sequences already disclosed in the past by the present inventors. By referring to FIG. 8A it will become obvious how the modular organization of the various silk proteins allows for a vast number of properties. Additionally, the effects of the sequences such as GPGGX are additive in nature. Specifically, the more repeats of GPGGX there are in a sequence, the more elastic will be the properties of the resulting fibers.

Relationships among Spider Silk Proteins

The Flagelliform sequences according to the present invention are distinguishable from the other spider silk proteins. Evaluating the three major modules in Flag as follows can summarize these differences:

GPGXX

While MaSp2, ADF-3, and ADF-4 also have GPGXX modules, Flag differs from these previously known silk proteins in many aspects:

1. Flag is predominantly GPGGX, with X being A, S, V, or Y 90% of the time.

2. MaSp2 is characterized by alternating GPGQQ and GPGGY. GPGQQ does not occur in Flag while GPGGY is only one of several options found in Flag.

3. ADF-3 is almost exclusively GPGQQ and GPGSGQQ. Neither of these motifs is found in Flag.

4. ADF-4 contains several variations on GPGXX (largely GPGGY, GPGSQ, and GPGGS) but its frequency of XX residues does not match Flag's.

5. No other silk protein has the large number (>43) of tandem GPGGX repeats found in Flag.

GGX

1. No previously known silk protein exhibits as many as 6 to 12 uninterrupted tandem GGX repeats, as observed in Flag.

2. The composition of the variable third residues is distinct in Flag. 96% of the X's in Flag are A, S, or T while:

in MaSp1 and ADF-2 they are largely A, L, Q or Y;

in ADF-1 and ADF-3 they are almost exclusively Y;

in MiSp1 they are A, Q and Y.

Spacer

The spacer sequence in Flag drastically differs in length, sequence, and amino acid composition from the spacer in MiSp1 and the putative spacer in ADF1. The only similarities between Flag's spacers and the other silk spacer domains are that they are relatively long repeats and occur rarely compared to the glycine and alanine repeats.

Flag spacer length=28 amino acids

MiSp1 spacer length=137 amino acids

ADF-1 spacer length=≧65 amino acids

Amino Acid Compositions (%) of the Spacer Regions from Flag, MiSp1, and ADF-1. For each spacer, the three most abundant amino acids are indicated by boldface

|   | Flag | MiSp1 | ADF-1 |
|---|------|-------|-------|
| A | 7.1 | 17.5 | 20.0 |
| D | 14.3 | 2.9 | 1.5 |
| E | 10.7 | 0.7 | 4.6 |
| F | — | 2.2 | 3.1 |
| G | 10.7 | 10.2 | 4.6 |
| H | — | 0.7 | 1.5 |
| I | 21.4 | 2.9 | 6.2 |
| L | 7.1 | 8.0 | 3.1 |
| M | — | 1.5 | 4.6 |
| N | — | 7.3 | 4.6 |
| P | 3.6 | 1.5 | 1.5 |
| Q | — | 2.9 | 1.5 |
| R | — | — | 6.2 |
| S | 7.1 | 24.1 | 21.5 |
| T | 14.3 | 7.3 | 9.2 |

-continued

|   | Flag | MiSp1 | ADF-1 |
|---|------|-------|-------|
| v | 3.6  | 7.3   | 1.5   |
| Y | —    | 2.9   | 4.6   |

Gly, Ala, Pro, Ser, Gln, and Tyr dominate spider silk proteins. The percentages of these amino acids are displayed for major ampullate and flagelliform translated silk GENES and extracted glandular silk PROTEINS (Andersen, *Comp. Biochem. Physiol.* 35, 705–711, 1970; Lewis, unpub.) The major ampullate glands are known to contain at least two distinct types of silk proteins (Nephila has MaSp1 and MaSp2, Araneus has ADF-3 and ADF-4). Note that MaSp1 and MaSp2 have different amino acid compositions, most notably in proline content. For each protein, the TOTAL of the combined percentages of the six amino acids is shown. The source spider species is listed below each protein composition graph (Araneus=*Araneus diadematus*, Nephila=*Nephila clavipes*)

TABLE 2a

OVERALL ACTUAL AND INFERRED AMINO ACID COMPOSITIONS
MAJOR AMPULLATE SILK (dragline, web frame, web radii)

|                   | % Gly | % Ala | % Pro | % Ser | % Gln | % Tyr | TOTAL |
|-------------------|-------|-------|-------|-------|-------|-------|-------|
| Nephila (gland)   | 45.8  | 22.2  | 3.5   | 7.4   | 10.9  | 4.3   | 94.1  |
| MaSp1             | 42.4  | 25.8  | 0.4   | 4.9   | 10.0  | 2.9   | 86.4  |
| MaSp2             | 30.9  | 21.1  | 13.6  | 10.0  | 11.8  | 4.8   | 92.2  |
| Araneus (gland)   | 37.2  | 17.6  | 15.8  | 7.4   | 11.5  | 3.9   | 93.4  |
| ADF-3             | 32.4  | 16.4  | 13.1  | 9.3   | 17.1  | 4.2   | 92.5  |
| ADF-4             | 27.6  | 20.7  | 12.4  | 17.6  | 4.4   | 4.4   | 87.1  |

TABLE 2b

FLAGELLIFORM SILK (elastic capture spiral)

|                 | % Gly | % Ala | % Pro | % Ser | % Gln | % Tyr | TOTAL |
|-----------------|-------|-------|-------|-------|-------|-------|-------|
| Araneus (gland) | 44.2  | 8.3   | 20.5  | 3.1   | 2.9   | 2.6   | 81.6  |
| Flag            | 48.8  | 7.4   | 14.4  | 9.0   | 0.8   | 4.8   | 85.2  |

The new flagelliform protein cDNA has answered many questions about silk protein structure. It strongly supports the proposition that β-turns are fundamental to providing elasticity (Hinman & Lewis, 1992, supra). In addition, through our model of gluten-like hydrogen bonding networks between β-spirals, Flag has corroborated the observed necessity of hydration for the capture silk (Vollrath & Edmonds, 1989, supra). Moreover, the lack of Ala-rich regions in a spider silk explains the NMR spectra indicating that flagelliform fibers may be entirely non-crystalline (Bonthrone et al., 1992, supra). By both complementing previous studies and revealing surprising sequence characteristics like patterned GPGGX variation, the flagelliform protein gene is key to understanding the basis of the elasticity of spider silks.

Evolution of the Spider Silk Gene Family

The modular affiliation hypothesis of silk protein evolution utilizes modular data (FIG. 6) to group silk proteins and provides useful clarification for structure-function analyses. For example, the presence or absence of the elastic module (GPGXX) divides the silk proteins into two groups. The silks with this module can be further subdivided into those with the strengthening poly-Ala crystalline module (MaSp2, ADF-3, ADF-4) and the one without (Flag).

Though the significance of the C-terminal regions in spider silk proteins has yet to be determined, the high sequence conservation among most of the known sequences could indicate an important functional role (Guerette et al., 1996, supra).

EXAMPLE 2

Expression of a cDNA Encoding a Polypeptide Comprising the Flagelliform Sequence In order to demonstrate expression of an engineered spider silk protein, the sequence from the flagelliform gland silk protein can be cloned into an *E. coli* expression vector. Other expressions systems including yeast and baculovirus are also contemplated. These types of expression systems are well known in the art.

Figure 7A:
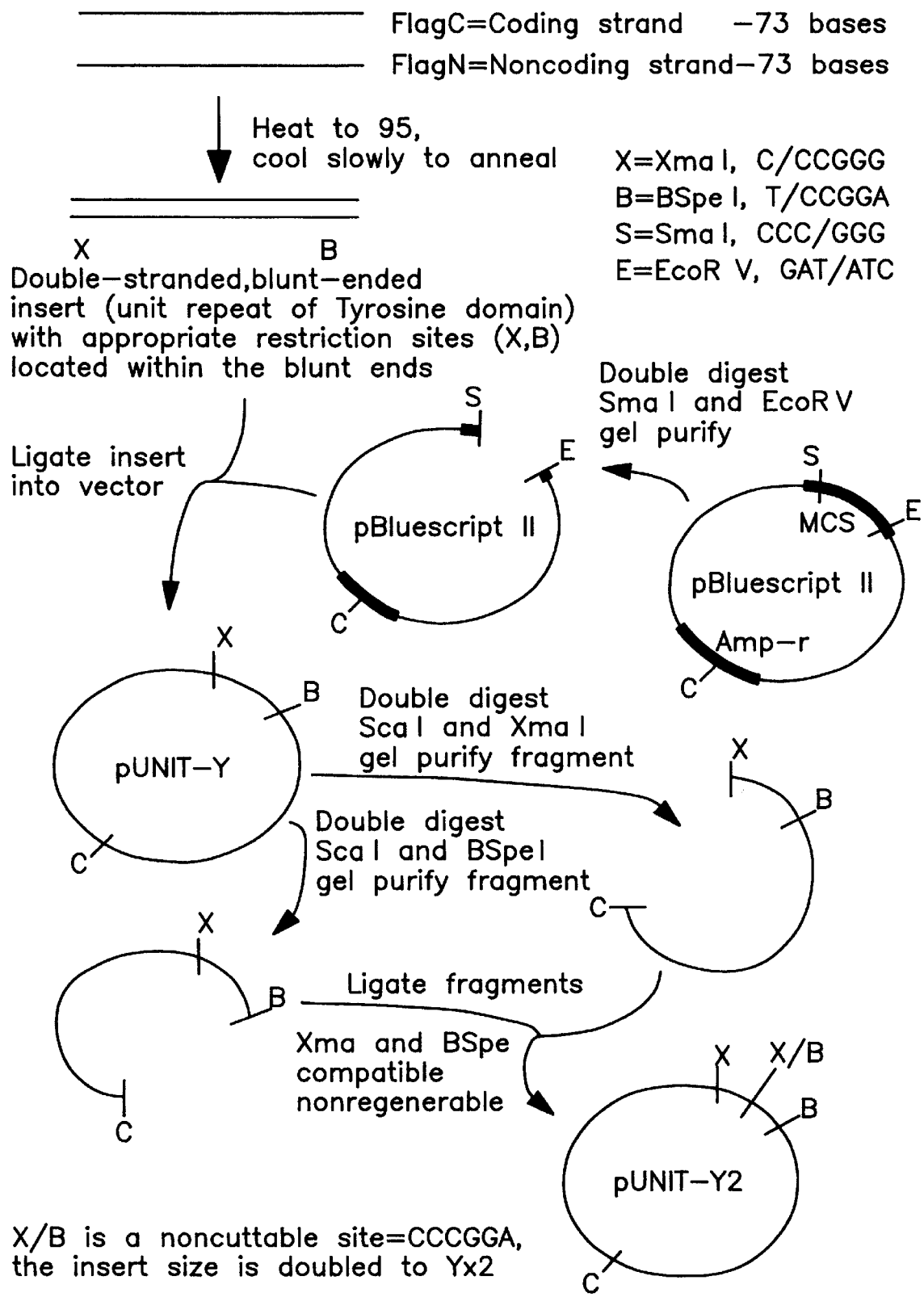
FIG. 7(a) (b) Construction strategy for the expression of flagelliform silk protein. SEQ.ID.NO.:6 comprises a nucleotide sequence of UNIT-Y and SEQ.ID.NO.:7 comprises the amino acid sequence of UNIT-Y. SEQ.ID.NO.:8 comprises a nucleotide sequence of UNIT-A and SEQ.ID.NO.:9 comprises the amino acid sequence of UNIT-A.
Figure 7B:
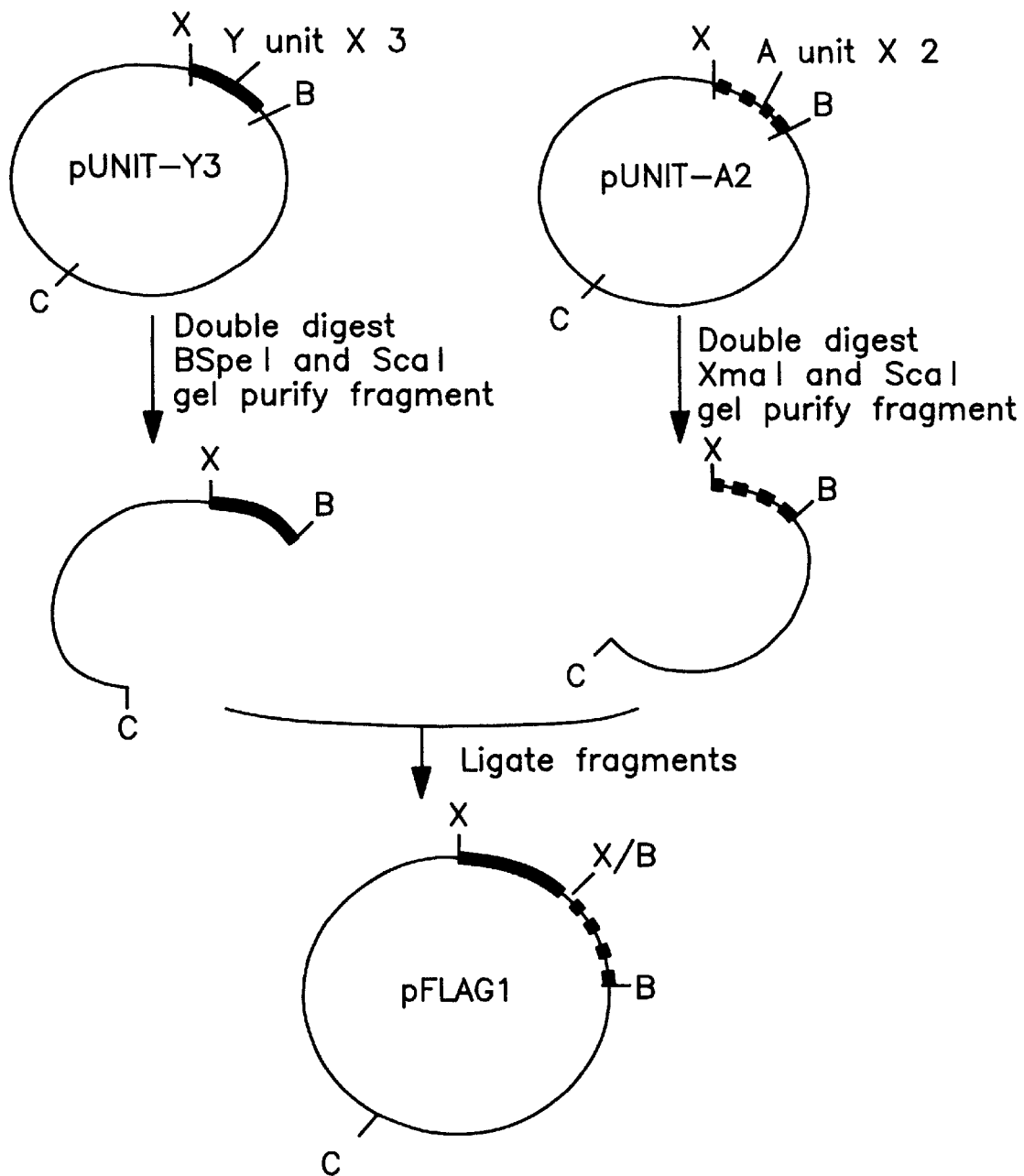
FIG. 7(c). Multimer formation. The pFLAG1 from the Construction strategy can be multiplied to form multimers (shown in FIG. 7(c) that repeat the large element containing three of the tyrosine domains with two of the alanine domains by using the same restriction endonuclease strategy used to construct the smaller repeats. At any stage, a "spacer" region can be inserted and then the process continued.
Figure 7C:
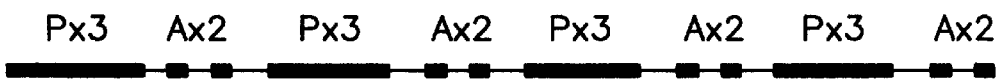

The construction strategy according to the present invention is described in FIGS. 7(a)–(c).

EXAMPLE 3

Preparation of Fibers From Spider Silk Proteins

The spider silk proteins can be viewed as derivatized polyamides. Accordingly, the methods for producing fiber from soluble spider silk proteins is similar to that used to produce typical polyamide fibers, e.g. nylons, and the like.

O'Brien et al. [supra] describe fiber production from adenovirus fiber proteins. In a typical fiber production, the spider silk proteins are solubilized in a strongly polar solvent. The protein solution is typically greater than 5% in protein concentration. The solution is preferably between 8 and 20% in protein.

Fibers are preferably spun from solutions demonstrating properties indicating a liquid crystal phase. The concentration at which the phase transition will occur is different for particular polypeptide compositions. However, the phase transition can be monitored by observing the clarity and birefrigence of the solution. A translucent appearance of the solution and the observation of birefringence detect onset of a liquid crystal phase when the solution is viewed through crossed polarizing filters.

The solvent used to dissolve the spider silk protein is preferably highly polar. Di- and tri- haloacetic acids, haloalcohols (e.g. hexafluoroisopropanol), exemplify such solvents. In some instances, co-solvents such as acetone are useful. Also, solutions of chaotropic agents, such as lithium thiocyanate, guanadine thiocyanate or urea can be used.

In one fiber-forming technique, fibers are first extruded from the protein solution through an orifice into methanol, until a length sufficient to be picked up by a mechanical means is produced. Then the fiber is pulled by such mechanical means through the methanol solution, collected and dried. The methods for drawing fibers are considered well known in the art. Fibers made from the 58 kDa synthetic MaSP consensus polypeptide, described in Example 2 of copending U.S. application Ser. No. 08/425,069, for instance, can be drawn by methods similar to those used for drawing low molecular weight nylons.

Industrial Applicability

The industrial applications of the present invention deal mainly with sutures for various medical procedures such as eye surgery, reconstructive surgery, vascular closure, bowel surgery, tympanic membrane, nerve reconstruction, cosmetic surgery, and central nervous system surgery; antibiotic impregnated sutures or implant material; matrix material for reconstuction of bone and connective tissue (could contain aggregated growth factors or cell attractants).

The invention being thus described various modifications of the materials and methods disclosed herein will be apparent to one of skill in the art. Such modifications are to be considered encompassed by the scope of the invention described by the claims below. Articles of the scientific and patent literature cited herein are incorporated by reference in their entirety by such citation.

Full Title References

Andersen, S. (1970) Amino acid composition of spider silks. *Comp. Biochem. Physiol.* 35, 705–711.

Beckwitt, R. & Arcidiacono, S. (1994) Sequence conservation in the C-terminal region of spider silk proteins (Spidroin) from *Nephila clavipes* (Tetragnathidae) and *Araneus bicentarius* (Araneidae). *J. Biol. Chem.* 269, 6661–6663.

Bonthrone, K., Vollrath, F., Hunter, B. & Sanders, J. (1992) The elasticity of spiders' web is due to water induced mobility at the molecular level. *Proc. R. Soc. Lond. B* 248, 141–144.

Coddington, J. (1989) Spinneret silk spigot morphology: evidence for the monophyly of orbweaving spiders, Cyrtophorinae (Araneidae), and the group Theridiidae plus Nesticidae. *J. Arachnol.* 17, 71–95.

Coddington, J. & Levi, H. (1991) Systematics and the evolution of spiders (Araneae). *Ann. Rev. Ecol. Syst.* 22, 565–592. Colgin, M. (1996) Structure and function of minor ampullate silk proteins from *Nephila clavipes*. Ph.D. thesis, University of Wyoming, Laramie.

Dong, Z., Lewis, R. & Middaugh, C. (1991) Molecular mechanism of spider silk elasticity. *Arch. Biochem. Biophys.* 284, 53–57.

Downing, D. (1996) Molecular modeling of vimentin filament assembly. *Proteins* 26, 472–478.

Emsley, P., Charles, I., Fairweather, N. & Isaacs, N. (1996) Structure of *Bordetella pertussis* virulence factor P.69 pertactin. *Nature* 381, 90–92.

Farris, J. (1989) The retention index and the rescaled consistency index. *Cladistics* 5, 417–419.

Gage, L. & Manning, R. (1976) Determination of the multiplicity of the silk fibroin gene and detection of fibroin gene-related DNA in the genome of *Bombyx mori*. *J. Mol. Biol.* 101, 327–348.

Glatz, L. (1972) Der spinnapparat haplogyner spinnen (Arachnida, Araneae). *Z. Morph. Tiere* 72, 1–25.

Gosline, J., Denny, M. & DeMont, M. (1984) Spider silk as rubber. *Nature* 309, 551–552.

Gosline, J., DeMont, M. & Denny, M. (1986) The structure and properties of spider silk. *Endeavour* 10, 37–43.

Gubler, U. & Hoffman, B. (1983) A simple and very efficient method for generating cDNA libraries. *Gene* 25, 263–269.

Guerette, P., Ginzinger, D., Weber, B. & Goslire, J. (1996) Silk properties determined by gland-specific expression of a spider fibroin gene family. *Science* 272, 112–115.

Henikoff, S. (1984) Unidirectional digestion with exonuclease III creates targeted breakpoints for DNA sequencing. *Gene* 28, 351–359.

Hinman, M. & Lewis, R. (1992) Isolation of a clone encoding a second dragline silk fibroin. *J. Biol. Chem.* 267, 19320–19324.

Hutchinson, E. & Thornton, J. (1994) A revised set of potentials for β-turn formation in proteins. *J. Prot. Sci.* 3, 2207–2216.

Kluge, A. & Farris, J. (1969) Quantitative phyletics and the evolution of anurans. *Syst. Zool.* 40, 117–130.

Köhler, T. & Vollrath, F. (1995) Thread biomechanics in the two orb-weaving spiders *Araneus diadematus* (Araneae, Araneidae) and *Uloborus walckenaerius* (Araneae, Uloboridae). *J. Exp. Zool.* 271, 1–17.

Kozak, M. (1984) Selection of initiation sites by eucaryotic ribosomes: effect of inserting AUG triplets upstream from the coding sequence for proinsulin. *Nuc. Acids Res.* 12, 3873–3893.

Kümmerlen, J., van Beek, J., Vollrath, F. & Meier, B. (1996) Local structure in spider dragline silk investigated by two-dimensional spin-diffusion nuclear magnetic resonance. *Macromol.* 29, 2920–2928.

Lewis, R. (1992) Spider silk: the unraveling of a mystery. *Accts. Chem. Res.* 25, 392–398.

Mita, K., Ichimura, S., Zama, M. & James, T. (1988) Specific codon usage pattern and its implications on the secondary structure of silk fibroin mRNA. *J. Mol. Biol.* 203, 917–925.

Mita, K., Ichimura, S. & James, T. (1994) Highly repetitive structure and its organization of the silk fibroin gene. *J. Mol. Evol.* 38, 583–592.

Nielsen, H., Engelbrecht, J., Brunak, S. & von Heijne, G. (1997) Identification of prokaryotic and eukaryotic signal peptides and prediction of their cleavage sites. *Prot. Eng.* 10, 1–6.

Nothwehr, S. & Gordon, J. (1990) Targeting of proteins into the eukaryotic secretory pathway: signal peptide structure/function relationships. *BioEssays* 12, 479–484.

Okayama, H. & Berg, P. (1982) High-efficiency cloning of full-length cDNA. *Mol. Cell Biol.* 2, 161–170.

Osaki, S. (1996) Spider silk as mechanical lifeline. *Nature* 384, 419.

Platnick, N., Coddington, J., Forster, R. & Griswold, C. (1991) Spinneret morphology and the phylogeny of haplogyne spiders (Araneae, Araneomorphae). *Am. Mus. Novit.* 3016, 1–73.

Rodriguez, R. & Candelas, G. (1995) Flagelliform or coronata glands of *Nephila clavipes*. *J. Exp. Zool.* 272, 275–280.

Simmons, A., Ray, E. & Jelinski, L. (1994) Solid-state $^{13}$C NMR of *Nephila clavipes* dragline silk establishes structure and identity of crystalline regions. *Macromol.* 27, 5235–5237.

Simmons, A., Michal, C. & Jelinski, L. (1996) Molecular orientation and two-component nature of the crystalline fraction of spider dragline silk. *Science* 271, 84–87.

Stauffer, S., Coguill, S. & Lewis, R. (1994) (Comparison of physical properties of three silks from *Nephila clavipes* and *Araneus gemmoides*. *J. Arachnol.* 22, 5–11.

Swofford, D. (1993) PAUP v.3.1.1. Smithsonian Institution, Washington, D.C.

Thiel, B., Kunkel, D. & Viney, C. (1994) Physical and chemical microstructure of spider dragline: a study by analystical transmission electron microscopy. *Biopolymers* 34, 1089–1097.

Urry, D., Luan, C.-H. & Peng, S. (1995) Molecular biophysics of elastin structure, function and pathology. *Ciba Found. Symp.* 192, 4–30.

Van Dijk, A., De Boef, E., Bekkers, A., Van Wijk, L., Van Swieten, E., Hamer, R. & Robillard, G. (1997a) Structure characterization of the central repetitive domain of high molecular weight gluten proteins. II. Characterization in solution and the dry state. *Prot. Sci.* 6, 649–656.

Van Dijk, A., Van Wijk, L., Van Vliet, A., Haris, P., Van Swieten, E., Tesser, G. & Robillard, G. (1997b) Structure characterization of the central repetitive domain of high molecular weight gluten proteins. I. Model studies using cyclic and linear peptides. *Prot. Sci.* 6, 637–648.

Vollrath, F. & Edmonds, D. (1989) Modulation of the mechanical properties of spider silk by coating with water. *Nature* 340, 305–307.

Wainwright, S., Biggs, W., Currey, J. & Goslirie, J. (1982) *Mechanical design in organisms*, Princeton University Press, Princeton.

Wasserman, Z. & Salemme, F. (1990) A molecular dynamics investigation of the elastomeric restoring forces in elastin. *Biopolymers* 29, 1613–1631.

Xu, M. & Lewis, R. (1990) Structure of a proteir superfiber: spider dragline silk. *Proc. Natl. Acad. Sci., USA* 87, 7120–7124.

Yoder, M. & Jurnak, F. (1995) The parallel β-helix and other coiled folds. *FASEB J.* 9, 335–342.

What is claimed is:

1. An isolated and purified flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-X)$_n$ wherein n is an integer of at least 4, wherein X is an amino acid, wherein 75 to 95% of X are selected from the group consisting of Ala, Ser, Tyr, and Val.

2. The protein of claim 1, wherein n is an integer greater than 9.

3. The protein of claim 1, wherein n is an integer greater than 43.

4. The protein of claim 1, wherein n is an integer between 43 and 63.

5. An isolated and purified flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Ala-Gly-Pro-Gly-Gly-Ala)$_n$ wherein n is an integer of at least 2.

6. An isolated and purified flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Ser-Gly-Pro-Gly-Gly-Tyr)$_n$ wherein n is an integer of at least 2.

7. An isolated and purified flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Tyr-Gly-Pro-Gly-Gly-Ser)$_n$ wherein n is an integer of at least 2.

8. An isolated and purified flagelliform gland silk fibroin protein originating from a flagelliform gland of an orb-web spinning spider, said silk fibroin protein comprising a glycine and proline rich repetitive βs region that forms β-spiral, said βs region represented by the following formula:

(Gly-Pro-Gly-Gly-Val-Gly-Pro-Gly-Gly-Ser)$_n$ wherein n is an integer of at least 2.

9. The protein of any one of claims 1, 5, 6, 7, wherein the silk fibroin protein further comprises a glycine rich Gr region that forms a 3$_{10}$-helix, said Gr region represented by the following formula:

(Gly-Gly-X)$_m$ wherein m is an integer of at least 1, wherein X is an amino acid, wherein 80–99% of X are selected from the group consisting of Ala, Ser, and Thr.

10. The protein of claim 9, wherein m is an integer between 1 and 20.

11. The protein of claim 9, wherein m is an integer between 6 and 12.

12. The protein of claim 9, wherein the protein comprises the amino acids residues depicted in SEQ ID NO:2.

13. The protein of claim 9, wherein the protein comprises the amino acids residues depicted in SEQ ID NO:4.

14. An isolated and purified protein comprising a glycine and proline rich repetitive βs region that forms a β-spiral, said βs region represented by the following formula:

(Gly-Pro-Gly-Gly-X)$_n$ wherein n is an integer of at least 4, wherein X is an amino acid, wherein 75 to 95% of X are selected from the group consisting of Ala, Ser, Tyr, and Val.

15. The protein of claim 14, wherein n is an integer greater than 9.

16. The protein of claim 14, wherein n is an integer greater than 43.

17. The protein of claim 14, wherein n is an integer between 43 and 63.

18. An isolated and purified protein comprising a glycine and proline rich repetitive βs region that forms a β-spiral, said βs region represented by the following formula:

(Gly-Pro-Gly-Gly-Ala-Gly-Pro-Gly-Gly-Ala)$_n$ wherein n is an integer of at least 2.

19. An isolated and purified protein comprising a glycine and proline rich repetitive βs region that forms a β-spiral, said βs region represented by the following formula:

(Gly-Pro-Gly-Gly-Ser-Gly-Pro-Gly-Gly-Tyr)$_n$ wherein n is an integer of at least 2.

20. An isolated and purified protein comprising a glycine and proline rich repetitive βs region that forms a β-spiral, said βs region represented by the following formula:

(Gly-Pro-Gly-Gly-Tyr-Gly-Pro-Gly-Gly-Ser)$_n$ wherein n is an integer of at least 2.

21. An isolated and purified protein comprising a glycine and proline rich repetitive βs region that forms a β-spiral, said βs region represented by the following formula:

(Gly-Pro-Gly-Gly-Val-Gly-Pro-Gly-Gly-Ser)$_n$ wherein n is an integer of at least 2.

22. The protein of any one of claims 17, 18, 19, 20, or 21, wherein the protein further comprises a glycine rich Gr region that forms a 3$_{10}$-helix, said Gr region represented by the following formula:

(Gly-Gly-X)$_m$ wherein m is an integer of at least 1, wherein X is an amino acid, wherein 80–99% of X are selected from the group consisting of Ala, Ser, and. Thr.

23. The protein of claim 22, wherein m is an integer between 1 and 20.

24. The protein of claim 22, wherein m is an integer between 6 and 12.

25. An isolated and purified protein having the formula:

[(Gly-Pro-Gly-Gly-X$_1$)$_n$ (Gly-Gly-X$_2$)$_m$ S (Gly-Gly-X$_2$)$_m$]$_p$ wherein n is an integer between 43 and 63, wherein X$_1$ is an amino acid, wherein 75 to 95% of X$_1$ are selected from the group consisting of Ala, Ser, Tyr, and Val;

wherein m is an integer between 3 and 12, wherein X$_2$ is an amino acid, wherein 80–99% of X$_2$ are selected from the group consisting of Ala, Ser, and Thr;

wherein S is an amino acid spacer sequence comprising 23 to 33 amino acids;

and p is an integer greater than 1.

26. The protein of claim 25, wherein S is selected from the group of amino acid sequences consisting of SEQ ID NO:15, SEQ ID NO:17, and SEQ ID:19.

27. An isolated and purified nucleic acid molecule encoding a flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-X)$_n$ wherein n is an integer of at least 4, wherein X is an amino acid, wherein 75 to 95% of X are selected from the group consisting of Ala, Ser, Tyr, and Val.

28. The nucleic acid molecule of claim 27, wherein n is an integer greater than 9.

29. The nucleic acid molecule of claim 27, wherein n is an integer greater than 43.

30. The nucleic acid molecule of claim 27, wherein n is an integer between 43 and 63.

31. An isolated and purified nucleic acid molecule encoding a flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Ala-Gly-Pro-Gly-Gly-Ala)$_n$ wherein n is an integer of at least 2.

32. An isolated and purified nucleic acid molecule encoding a flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Ser-Gly-Pro-Gly-Gly-Tyr)$_n$ wherein n is an integer of at least 2.

33. An isolated and purified nucleic acid molecule encoding a flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Tyr-Gly-Pro-Gly-Gly-Ser)$_n$ wherein n is an integer of at least 2.

34. An isolated and purified nucleic acid molecule encoding a flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-Val-Gly-Pro-Gly-Gly-Ser)$_n$ wherein n is an integer of at least 2.

35. The nucleic acid molecule of any one of claim 30, 31, 32, 33, or 34, wherein the silk fibroin protein further comprises a glycine rich Gr region that forms a 3$_{10}$-helix, said Gr region represented by the following formula:

(Gly-Gly-X)$_m$ wherein m is an integer of at least 1, wherein X is an amino acid, wherein 80–99% of X are selected from the group consisting of Ala, Ser, and Thr.

36. The nucleic acid molecule of claim 35, wherein m is an integer between 1 and 20.

37. The nucleic acid molecule of claim 35, wherein m is an integer between 6 and 12.

38. The nucleic acid molecule of claim 35, wherein the silk fibroin protein comprises the amino acids residues depicted in SEQ ID NO:2.

39. The nucleic acid molecule of claim 38, wherein the nucleic acid molecule comprises the nucleotides depicted in SEQ ID NO:1.

40. The nucleic acid molecule of claim 35, wherein the silk fibroin protein comprises the amino acids residues depicted in SEQ ID NO:4.

41. The nucleic acid molecule of claim 40, wherein the nucleic acid molecule comprises the nucleotides depicted in SEQ ID NO:3.

42. An isolated and purified nucleic acid molecule encoding protein comprising a glycine and proline rich repetitive βs region that forms a β-spiral, said βs region represented by the following formula:

(Gly-Pro-Gly-Gly-X)$_n$ wherein n is an integer of at least 4, wherein X is an amino acid, wherein 75 to 95% of X are selected from the group consisting of Ala, Ser, Tyr, and Val.

43. The nucleic acid molecule of claim 42, wherein n is an integer greater than 9.

44. The nucleic acid molecule of claim 42, wherein n is an integer greater than 43.

45. The nucleic acid molecule of claim 42, wherein n is an integer between 43 and 63.

46. The nucleic acid molecule of claim 42, wherein the silk fibroin protein further comprises a glycine rich Gr region that forms a 3$_{10}$-helix, said Gr region represented by the following formula:

(Gly-Gly-X)$_m$ wherein m is an integer of at least 1, wherein X is an amino acid, wherein 80–99% of X are selected from the group consisting of Ala, Ser, and Thr.

47. The nucleic acid molecule of claim 46, wherein m is an integer between 1 and 20.

48. The nucleic acid molecule of claim 46, wherein m is an integer.

49. An isolated and purified nucleic acid molecule encoding a protein having the formula:

[(Gly-Pro-Gly-Gly-X$_1$)$_n$ (Gly-Gly-X$_2$)$_m$S (Gly-Gly-X$_2$)$_m$ ]$_p$ wherein n is an integer between 43 and 63, wherein X$_1$ is an amino acid, wherein 75 to 95% of X$_1$ are selected from the group consisting of Ala, Ser, Tyr, and Val, wherein m is an integer between 3 and 12, wherein X$_2$ is an amino acid, wherein 80–99% of X$_2$ are selected from the group consisting of Ala, Ser, and Thr, wherein S is an amino acid spacer sequence comprising 23 to 33 amino acids, and wherein p is an integer greater than 1.

50. The nucleic acid molecule of claim 49, wherein S is selected from the group of amino acid sequences consisting of SEQ ID NO:15, SEQ ID NO:17, and SEQ ID NO:19.

51. An expression vector comprising the nucleic acid molecule encoding the protein of claim 27.

52. An expression vector comprising the nucleic acid molecule encoding the protein of claim 35.

53. An expression vector comprising the nucleic acid molecule encoding the protein of claim 38.

54. An expression vector comprising the nucleic acid molecule encoding the protein of claim 40.

55. An expression vector comprising the nucleic acid molecule encoding the protein of claim 42.

56. An expression vector comprising the nucleic acid molecule encoding the protein of claim 46.

57. An expression vector comprising the nucleic acid molecule encoding the protein of claim 49.

58. A host cell transformed with the expression vector of claim 51.

59. A host cell transformed with the expression vector of claim 52.

60. A host cell transformed with the expression vector of claim 53.

61. A host cell transformed with the expression vector of claim 54.

62. A host cell transformed with the expression vector of claim 55.

63. A host cell transformed with the expression vector of claim 56.

64. A host cell transformed with the expression vector of claim 57.

65. A method of making a recombinant flagelliform gland silk fibroin protein originating from a flagelliform gland of an orb-web spinning spider, said silk fibroin protein comprising a glycine and proline rich repetitive βs region that forms a β-spiral, said βs region represented by the following formula:

(Gly-Pro-Gly-Gly-X)$_n$ wherein n is an integer of at least 4, wherein X is an amino acid, wherein 75 to 95% of X are selected from the group consisting of Ala, Ser, Tyr, and Val, said method comprising culturing the host cell of claim 58 under conditions which result in the expression of the recombinant protein and isolating the recombinant protein therefrom.

66. A method of making a recombinant silk fibroin protein comprising a βs region and a glycine rich Gr region, said protein represented by the following formula:

(Gly-Pro-Gly-Gly-X$_1$)$_n$ (Gly-Gly-X$_2$)$_m$ wherein n is an integer of at least 4, wherein X$_1$ is an amino acid, wherein 75 to 95% of X$_1$ are selected from the group consisting of Ala, Ser, Tyr, and Val, wherein m is an integer of at least 1, wherein X$_2$ is an amino acid, wherein 80–99% of X$_2$ are selected from the group consisting of Ala, Ser, and Thr, said method comprising culturing the host cell of claim 59 under conditions which result in the expression of the recombinant protein and isolating the recombinant protein therefrom.

67. A method of making a flagelliform gland silk fibroin protein originating from a flagelliform gland of an orb-web spinning spider, said silk fibroin protein comprising the amino acids residues depicted in SEQ ID NO:2, said method comprising culturing the host cell of claim 60 under conditions which result in the expression of the recombinant protein and isolating the recombinant protein therefrom.

68. A method of making a flagelliform gland silk fibroin protein originating from a flagelliform gland of an orb-web spinning spider, said silk fibroin protein comprising the amino acid residues depicted in SEQ ID NO:4, said method comprising culturing the host cell of claim 61 under conditions which result in the expression of the recombinant protein and isolating the recombinant protein therefrom.

69. A method of making a protein comprising a glycine and proline rich repetitive βs region that forms a β-spiral, said βs region represented by the following formula:

(Gly-Pro-Gly-Gly-X)$_n$ wherein n is an integer of at least 4, wherein X is an amino acid, wherein 75 to 95% of X are selected from the group consisting of Ala, Ser, Tyr, and Val, said method comprising culturing the host cell of claim 62 under conditions which result in the expression of the recombinant protein and isolating the recombinant protein therefrom.

70. A method of making a recombinant protein comprising a βs region and a glycine rich Gr region, said protein represented by the following formula:

(Gly-Pro-Gly-Gly-X$_1$)$_n$ (Gly-Gly-X$_2$)$_m$ wherein n is an integer of at least 4, wherein X$_1$ is an amino acid, wherein 75 to 95% of X$_1$ are selected from the group consisting of Ala, Ser, Tyr, and Val, wherein m is an integer of at least 1, wherein X$_2$ is an amino acid, wherein 80–99% of X$_2$ are selected from the group consisting of Ala, Ser, and Thr, said method comprising culturing the host cell of claim 63 under conditions which result in the expression of the recombinant protein and isolating the recombinant protein therefrom.

71. A method of making a recombinant protein having the formula:

[(Gly-Pro-Gly-Gly-X$_1$)$_n$ (Gly-Gly-X$_2$)$_m$ S (Gly-Gly-X$_2$)$_m$]$_p$ wherein n is an integer between 43 and 63, wherein X$_1$ is an amino acid, wherein 75 to 95% of X$_1$ are selected from the group consisting of Ala, Ser, Tyr, and Val, wherein m is an integer between 3 and 12, wherein X$_2$ is an amino acid, wherein 80–99% of X$_2$ are selected from the group consisting of Ala, Ser, and Thr, wherein S is an amino acid spacer sequence comprising 23 to 33 amino acids, and wherein p is an integer greater than 1, said method comprising culturing the host cell of claim 64 under conditions which result in the expression of the recombinant protein and isolating the recombinant protein therefrom.

* * * * *